United States Patent
Urano et al.

(10) Patent No.: US 9,784,732 B2
(45) Date of Patent: Oct. 10, 2017

(54) ACIDIC ENVIRONMENT-DETECTING FLUORESCENT PROBE

(75) Inventors: Yasuteru Urano, Tokyo (JP); Tetsuo Nagano, Tokyo (JP); Daisuke Asanuma, Tokyo (JP); Kenzo Hirose, Tokyo (JP); Shigeyuki Namiki, Tokyo (JP); Yousuke Takaoka, Tokyo (JP)

(73) Assignee: THE UNIVERSITY OF TOKYO, Tokyo (JP)

( * ) Notice: Subject to any disclaimer, the term of this patent is extended or adjusted under 35 U.S.C. 154(b) by 188 days.

(21) Appl. No.: 14/343,033

(22) PCT Filed: Sep. 6, 2012

(86) PCT No.: PCT/JP2012/072688
§ 371 (c)(1),
(2), (4) Date: Apr. 18, 2014

(87) PCT Pub. No.: WO2013/035767
PCT Pub. Date: Mar. 14, 2013

(65) Prior Publication Data
US 2014/0248654 A1    Sep. 4, 2014

(30) Foreign Application Priority Data

Sep. 7, 2011 (JP) .................. 2011-194652
Mar. 2, 2012 (JP) .................. 2012-046922

(51) Int. Cl.
| | | |
|---|---|---|
| *C07D 311/82* | (2006.01) | |
| *C07D 405/10* | (2006.01) | |
| *C07D 405/14* | (2006.01) | |
| *G01N 33/52* | (2006.01) | |
| *C09K 11/06* | (2006.01) | |
| *C07D 405/04* | (2006.01) | |
| *C09B 11/24* | (2006.01) | |
| *G01N 33/50* | (2006.01) | |
| *C09B 69/00* | (2006.01) | |
| *C09B 69/10* | (2006.01) | |
| *G01N 21/64* | (2006.01) | |

(52) U.S. Cl.
CPC ........... *G01N 33/52* (2013.01); *C07D 311/82* (2013.01); *C07D 405/04* (2013.01); *C07D 405/14* (2013.01); *C09B 11/24* (2013.01); *C09B 69/00* (2013.01); *C09B 69/103* (2013.01); *C09K 11/06* (2013.01); *G01N 33/5005* (2013.01); *C09K 2211/1044* (2013.01); *C09K 2211/1088* (2013.01); *G01N 21/6428* (2013.01)

(58) Field of Classification Search
None
See application file for complete search history.

(56) References Cited

FOREIGN PATENT DOCUMENTS

| | | |
|---|---|---|
| WO | 2008/059910 | 5/2008 |
| WO | 2008/059916 A1 | 5/2008 |
| WO | WO 2010/033011 | * 3/2010 |

OTHER PUBLICATIONS

Wu et al. (2008). Synthesis and Spectroscopic Properties of Rosamines with Cyclic Amine Substituents. Journal of Organic Chemistry, v73, p. 8711-8718).*
Urano, Y., et al., Nat. Med., Selective molecular imaging of viable cancer cells with pH-activatable fluorescence probes, vol. 15(1), pp. 104-109, 2009.
International Search Report issued in International Application No. PCT/JP2012/072668, dated Oct. 2, 2012.

* cited by examiner

*Primary Examiner* — Emily Bernhardt
(74) *Attorney, Agent, or Firm* — Knobbe, Martens, Olson & Bear, LLP.

(57) ABSTRACT

Provided is a compound represented by formula (I), which can be used as a fluorescent probe that becomes highly fluorescent only in an intracellular acidic environment and can be adapted to the fluorescent imaging of an intracellular vesicle that is a microstructure.

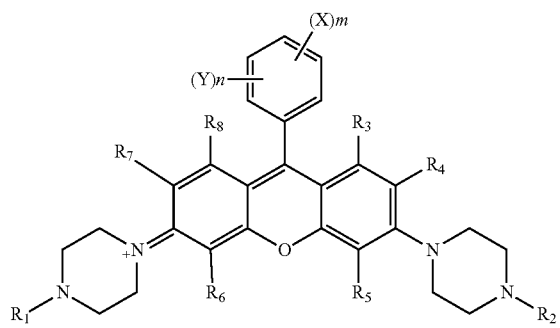

In the formula, $R_1$ and $R_2$ independently represent a hydrogen atom, or an alkyl group which may be substituted (wherein $R_1$ and/or $R_2$ represents an alkyl group which may be substituted); $R_3$, $R_4$, $R_5$, $R_6$, $R_7$ and $R_8$ independently represent a hydrogen atom, a halogen atom, or the like; X represents a functional group to which a labeling site or a target-accumulating site can be introduced, or the like; Y represents a halogen atom, an alkyl group which may be substituted, or the like; m represents an integer of 0 to 5; and n represents an integer of 0 to 5.

6 Claims, 12 Drawing Sheets

[Figure 1-1]
FIG. 1 − 1
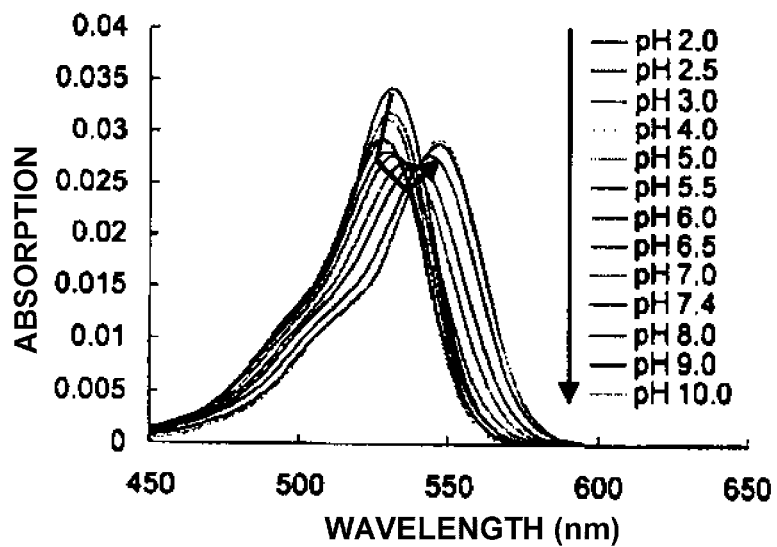
[Figure 1-2]
FIG. 1 − 2
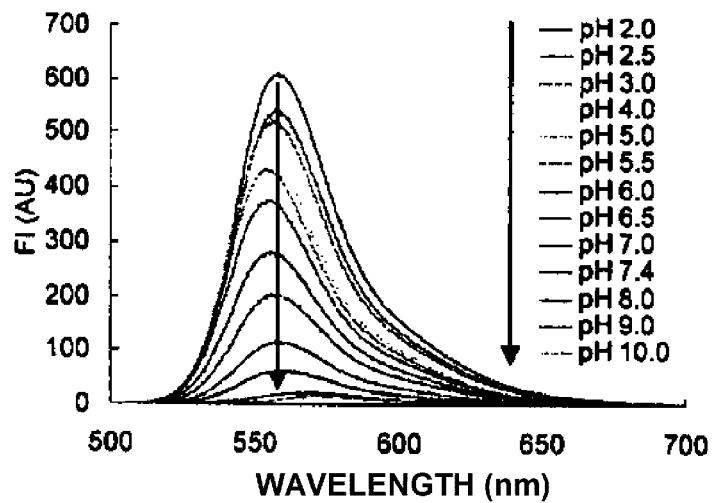

[Figure 1-3]
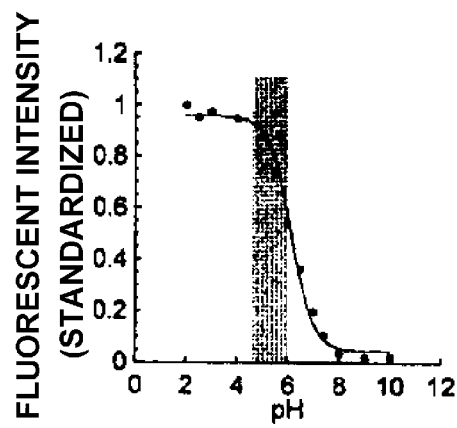
FIG. 1 — 3
[Figure 2]
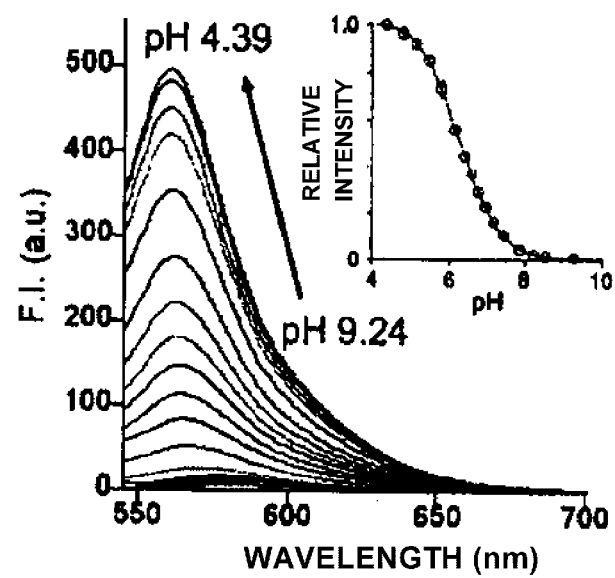
FIG. 2

[Figure 3]
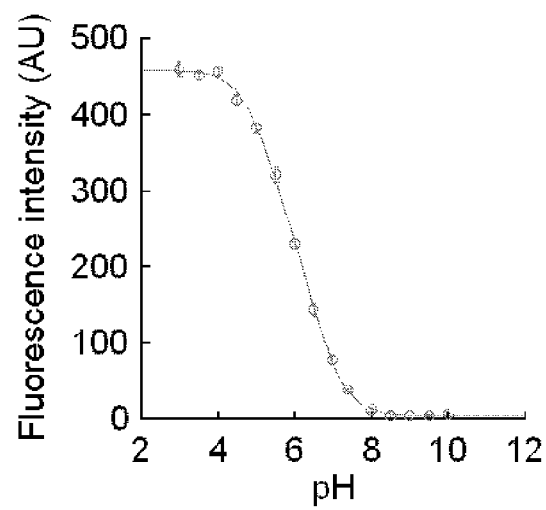
[Figure 4-1]
FIG. 4 − 1
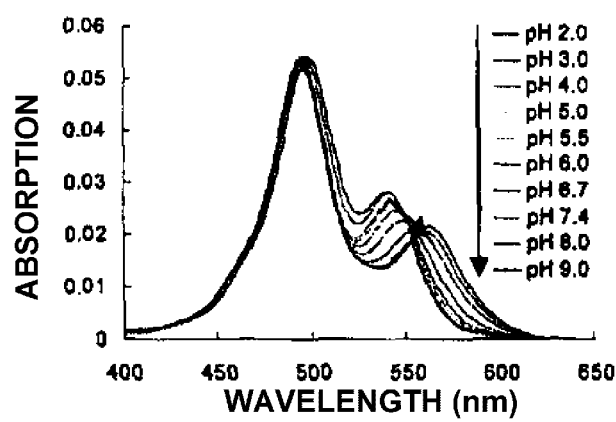

[Figure 4-2]
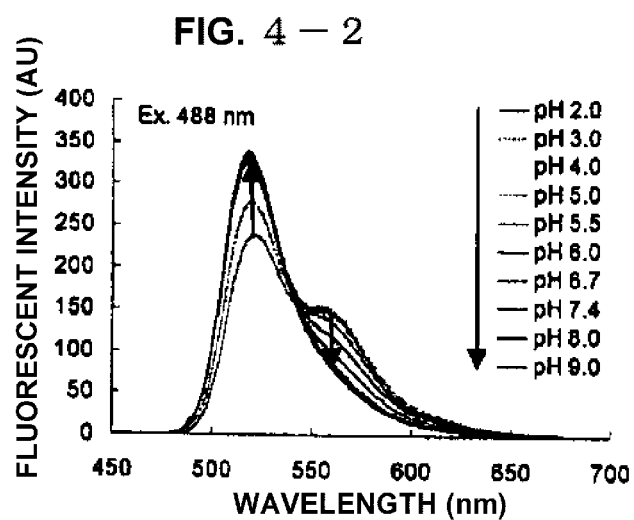
[Figure 4-3]
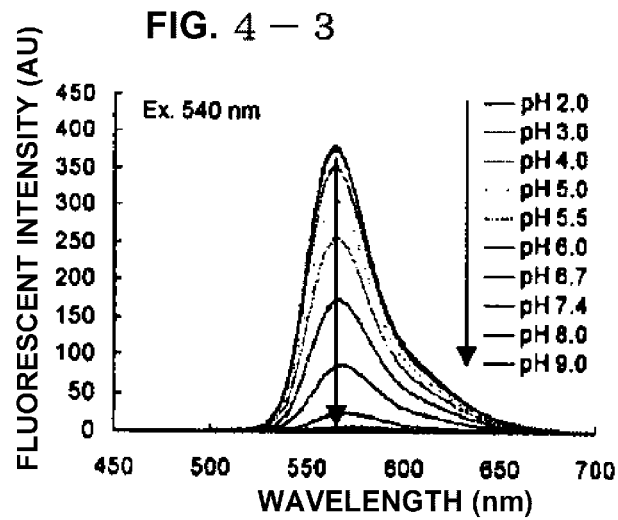

[Figure 4-4]
FIG. 4 − 4
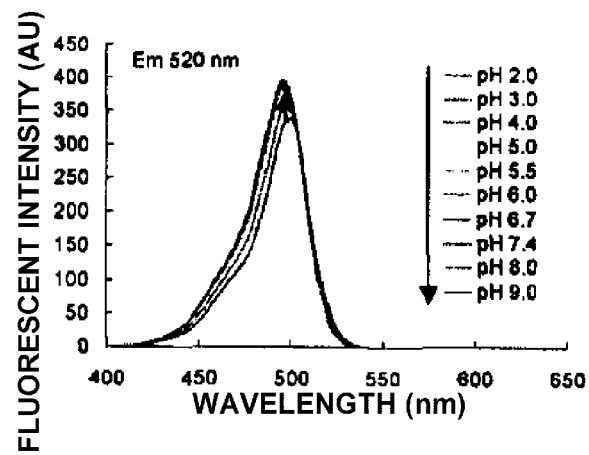
[Figure 4-5]
FIG. 4 − 5
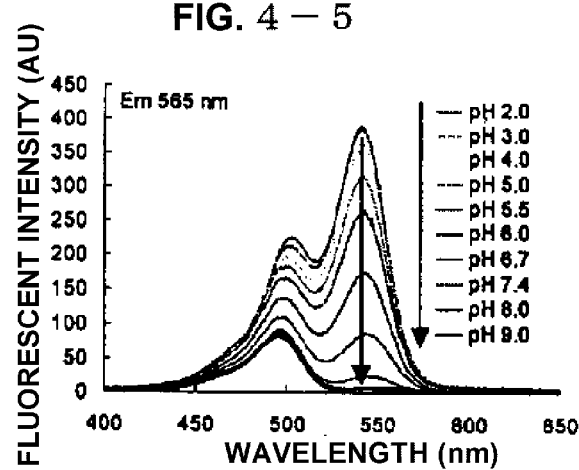

[Figure 9]
FIG. 9
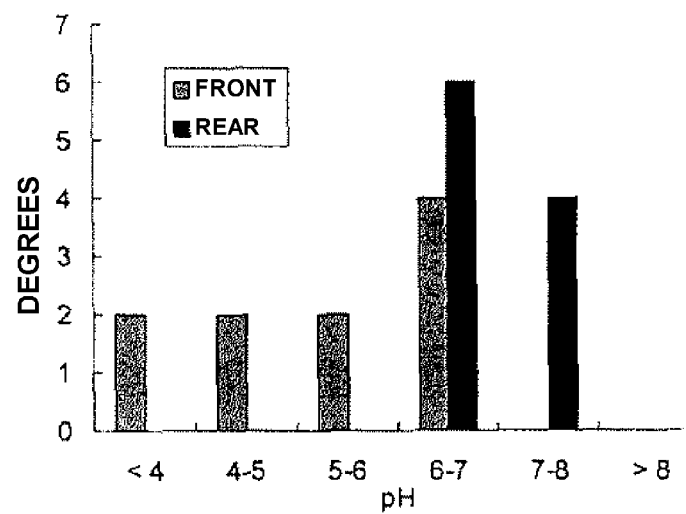
[Figure 10]
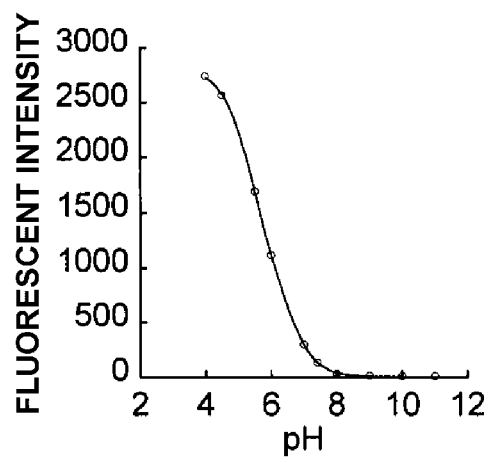

[Figure 11]
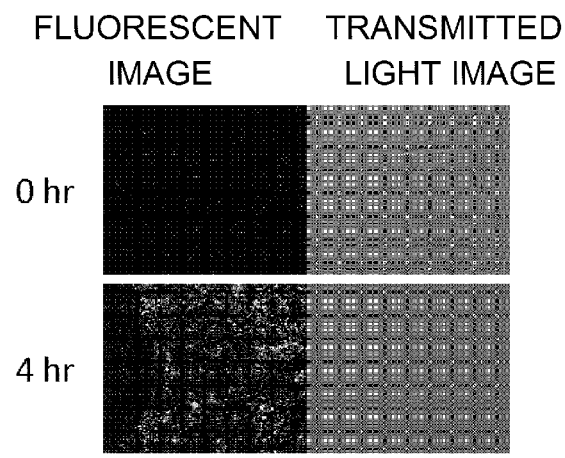
[Figure 12]
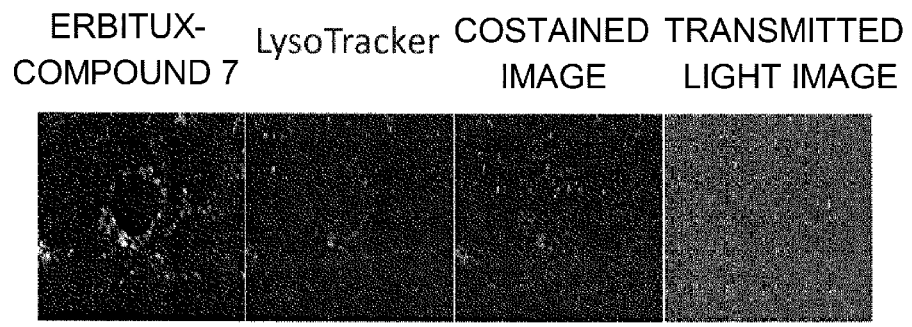

[Figure 13-1]
FIG. 1 3 − 1
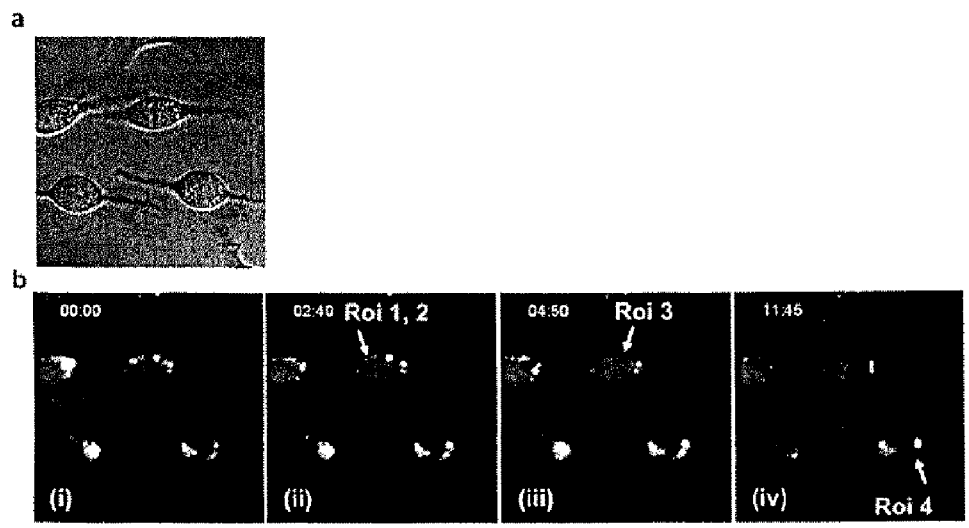
[Figure 13-2]
FIG. 1 3 − 2
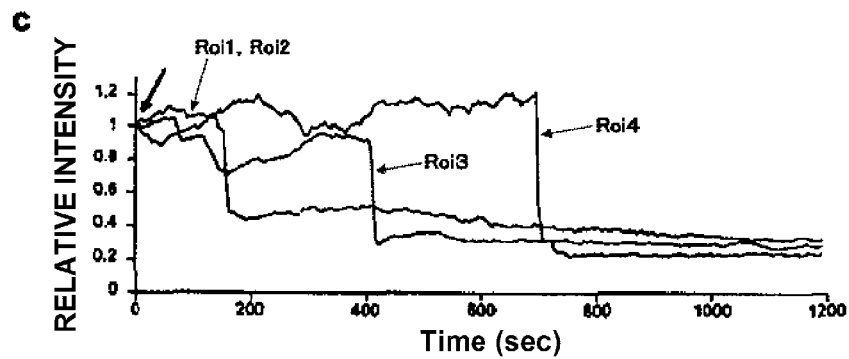

[Figure 14-1]
FIG. 1 4 − 1
[Figure 14-2]
FIG. 1 4 − 2
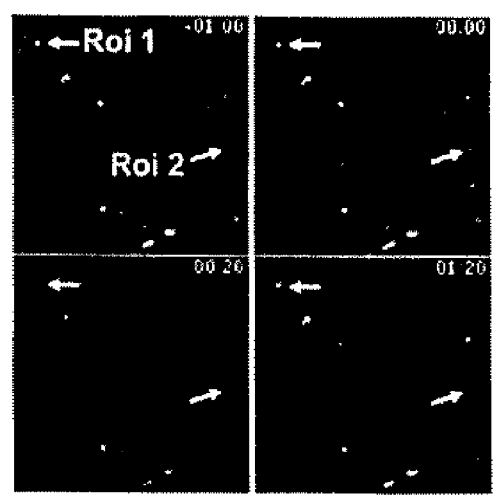

[Figure 14-3]
FIG. 14-3
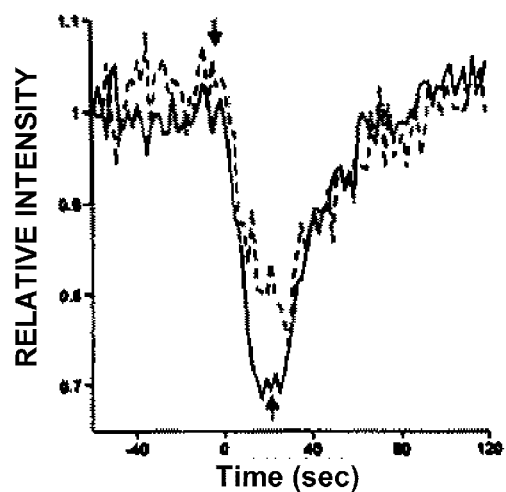
[Figure 15]
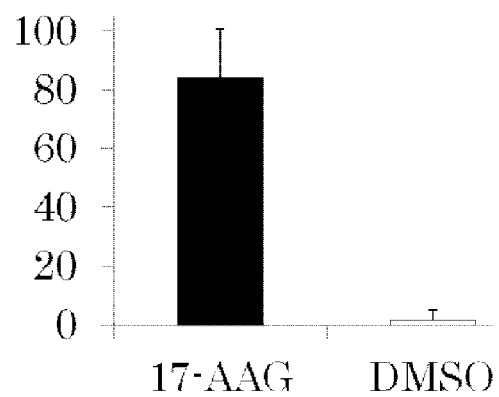
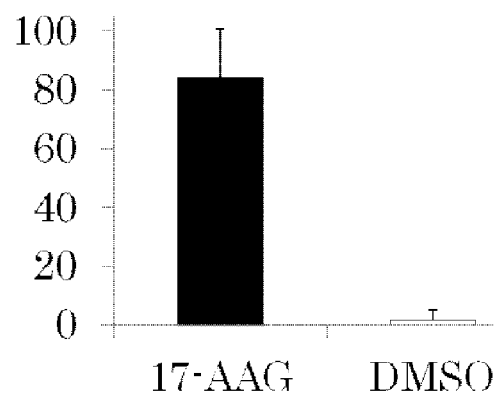

ACIDIC ENVIRONMENT-DETECTING FLUORESCENT PROBE

CROSS REFERENCE TO RELATED APPLICATIONS

This application is the U.S. National Phase of International Application No. PCT/JP2012/072688, filed Sep. 6, 2012, designating the U.S. and published as WO/2013/035767 on Mar. 14, 2013 which claims the benefit of Japanese Patent Applications No. 2011-194652, filed Sep. 7, 2011 and No. 2012-046922, filed Mar. 2, 2012.

TECHNICAL FIELD

The present invention relates to a fluorescent probe capable of altering fluorescence properties in an intracellular acidic environment. The present invention also relates to a fluorescent probe imparted with functionality matched to observed cellular phenomena via the introduction of a labeling site or an acidic organelle accumulation site into the fluorescent probe.

BACKGROUND ART

Known cellular phenomena related to acidic organelles include endocytosis, exocytosis, and autophagy, and acidic pHs within intracellular vesicles during these processes are known to affect vesicular membrane transport and hydrolase activity within the vesicular lumina, and, by extension, playing a major role in cellular functioning. The development of techniques of measuring intracellular vesicular pH is desirable in order to understand these phenomena, and pH probes that alter fluorescence properties in acidic environments promise to be useful tools.

The inventors have previously developed various pH probes using a BODIPY fluorophore (Urano, Y. et al., Nat. Med. 15, 104, 2009; WO/2008/059910). However, performing high-magnification observation of the microscopic structures of intracellular vesicles requires high-intensity excitation light, which causes these pH probes to fade, impeding pH measurement.

As such, there are as of yet no reports of a photostable pH probe that only exhibits strong fluorescence within intracellular acidic environments and is capable of withstanding fluorescent imaging of the microscopic structures of intracellular vesicles.

PRIOR ART REFERENCES

Patent References

Patent Reference 1: WO 2008/059910

Non-Patent References

Non-Patent Reference 1: Urano, Y. et al., Nat. Med. 15, 104, 2009

SUMMARY OF THE INVENTION

An object of the present invention is to develop a fluorescent probe that only exhibits strong fluorescence within intracellular acidic environments and is capable of withstanding fluorescent imaging of the microscopic structures of intracellular vesicles—features that have not been achieved in the prior art—thereby enabling fluorescent imaging of acidic pHs in acidic organelles. Another object of the invention is to develop a technique of enabling fluorescent imaging matching the cellular phenomenon being observed, such as endocytosis or exocytosis.

The inventors engaged in various investigations into the hypothesis that developing a pH probe having a core of a fluorophore of superior resistance to light-induced fading, such as Rhodamine, might enable measurement of acidic organelle pH.

pHrodo™ (structure not publicly available) and Rhosamine 5h have previously been reported as pH probes having Rhodamine cores. However, at a pKa of 7.3, the region in which pHrodo™ exhibits changes in fluorescence is near neutral, and Rhosamine 5h, although its pKa has not been reported, similarly has a fluorescence change region near neutral. In either case, changes in intracellular acidic environment cannot be captured with sensitivity.

As the result of dedicated research into developing a fluorescent probe that alters fluorescence properties in intracellular acidic environments generally of pH 4.5-6.0, the inventors succeeded in developing a fluorescent probe that only exhibits strong fluorescence in intracellular acidic environment via the use of Rhodamine as a core and the introduction of an N-alkyl piperidinyl group into the molecule.

The inventors also discovered that it is possible, in the fluorescent probe according to the present invention, to impart the fluorescent probe with functionality matching the cellular phenomena being observed via the introduction of a labeling site or a target-accumulating site (acidic organelle accumulation site).

Specifically, the present invention relates to:

(1) A compound represented by the following general formula (I):

[Formula 1]

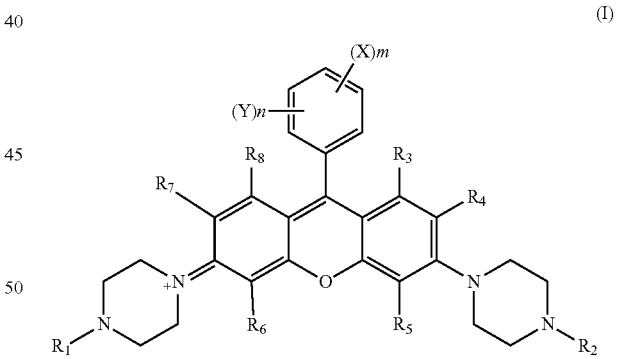

(wherein $R_1$ and $R_2$ each independently represent hydrogen or an optionally substituted alkyl group (at least one of $R_1$ and $R_2$ being an optionally substituted alkyl group); $R_3$, $R_4$, $R_5$, $R_6$, $R_7$, and $R_8$ each independently represent hydrogen, a halogen, or an optionally substituted alkyl group; X represents a functional group into which a labeling site or a target-accumulating site can be introduced, or a substituent into which a labeling site or a target-accumulating site has been introduced; Y represents a halogen, an optionally substituted alkyl group, an optionally substituted alkoxyl group, or a cyano group; m represents an integer from 0 to 5; X may optionally be identical or different when m is 2 or higher; n represents an integer from 0 to 5; and Y may optionally be identical or different when n is 2 or higher; and the sum of m and n being an integer equal to 5 or less) or a salt thereof;

(2) the compound or salt thereof according to (1), wherein each of $R_1$ and/or $R_2$ in general formula (I) is an optionally substituted $C_{1-4}$ alkyl group;

(3) the compound or salt thereof according to (1) or (2), wherein the functional group into which a labeling site or a target-accumulating site can be introduced is at least one group selected from the group consisting of a carboxyl group, a carboxyl group-comprising alkyl group, an amino group, an amide group, a maleimide group, a maleimide group-comprising alkyl group, an isothiocyanate group, a sulfonyl chloride group, a haloalkyl group, a haloacetamide group, an azide group, and an alkynyl group;

(4) the compound or salt thereof according to any one of (1)-(3), wherein the substituent into which a labeling site or a target-accumulating site has been introduced is represented by —(X'-T-S) (wherein X' represents a group into which a labeling site or target-accumulating site is introduced; T, when present, represents a crosslinking group; and S represents a labeling site or target-accumulating site), and m is at least 1;

(5) the compound or salt thereof according to (4), wherein the group into which a labeling site or target-accumulating site is introduced of X' is a carbonyl group, an alkyl carbonyl group, an amino group, an alkylamino group, an amide group, an isothiocyanate group, a sulfonyl chloride group, a haloalkyl group, a haloacetamide group, an azide group, or an alkynyl group;

(6) the compound or salt thereof according to (4) or (5), wherein S is an N-hydroxysuccinimide ester, a HaloTag ligand, a weakly basic amine, a polyethylene glycol group optionally comprising a modifying group at one or both terminals, a maleimide, an isothiocyanate group, a sulfonyl chloride group, a haloalkyl group, a haloacetamide group, an azide group, an alkynyl group, a benzylguanine derivative, or a benzylcytosine derivative;

(7) a fluorescent probe containing the compound or salt thereof according to any one of (1)-(6);

(8) a method of measuring intracellular acidic regions, the method comprising steps of:
(a) introducing the compound or salt thereof according to any one of (1)-(6) into a cell; and
(b) measuring fluorescence emitted within the cell by the compound or salt thereof; and (9) the method according to (8), wherein acidic regions in which intracellular acidic organelles are present are measured.

The compound represented by general formula (I) of the present invention only exhibits strong fluorescence in intracellular acidic environments, and is therefore capable of fluorescent detection of intracellular acidic environments. In addition, the compound represented by general formula (I) has superior photostability, and is therefore capable of withstanding fluorescent imaging of the microstructures of intracellular vesicles. Accordingly, pH changes in intracellular microstructures can be observed in real-time using the fluorescent probe according to the present invention. In addition, a compound constituted by the compound represented by general formula (I) into which a labeling site or a target-accumulating site has been introduced allows for the real-time visualization of various phenomena related to intracellular acidic vesicles.

BRIEF DESCRIPTION OF THE DRAWINGS

FIG. 1-1 shows changes in absorption spectrum exhibited when pH is changed from 10.0 to 2.0 in 200 mM of a phosphate buffer solution of Compound A (the direction of the arrow in the graph indicating an increase of solution pH).

FIG. 1-2 shows changes in fluorescence spectrum exhibited when pH is changed from 10.0 to 2.0 in 200 mM of a phosphate buffer solution of Compound A (the direction of the arrow in the graph indicating an increase of solution pH).

FIG. 1-3 shows the pH profile of the fluorescent intensity of Compound A.

FIG. 2 shows changes in fluorescence spectrum and pH profile exhibited when pH is changed from 9.24 to 4.39 in 100 mM of a phosphate buffer solution of Compound 1 (the direction of the arrow in the graph indicating a decrease of solution pH).

FIG. 3 shows the pH profile of the fluorescent intensity of Compound D.

FIG. 4-1 shows changes in absorption spectrum exhibited when pH is changed from 9.0 to 2.0 in 200 mM of a phosphate buffer solution of Dye Conjugate 1 (Dex-compound B&A 488).

FIG. 4-2 shows changes (excitation wavelength: 488 nm) in fluorescence emission spectrum exhibited when pH is changed from 9.0 to 2.0 in 200 mM of a phosphate buffer solution of Dye Conjugate 1.

FIG. 4-3 shows changes (excitation wavelength: 540 nm) in fluorescence emission spectrum exhibited when pH is changed from 9.0 to 2.0 in 200 mM of a phosphate buffer solution of Dye Conjugate 1.

FIG. 4-4 shows changes (emission wavelength: 520 nm) in fluorescence excitation spectrum exhibited when pH is changed from 9.0 to 2.0 in 200 mM of a phosphate buffer solution of Dye Conjugate 1.

FIG. 4-5 shows changes (emission wavelength: 565 nm) in fluorescence excitation spectrum exhibited when pH is changed from 9.0 to 2.0 in 200 mM of a phosphate buffer solution of Dye Conjugate 1.

FIG. 5 shows the pH profile for the fluorescent intensity of Dye Conjugate 1.

FIG. 9 is a histogram showing calculated pH values for individual lysosomes (n=10) before and after $NH_4Cl$ treatment.

FIG. 10 shows fluorescent intensity against pH for an Erbitux-compound 7 conjugate.

FIG. 11 is a photograph of the results of imaging cells of the EGFR-overexpressing A431 cell line using an Erbitux-compound 7 conjugate.

FIG. 12 is a photograph of the results of imaging cells of the EGFR-overexpressing A431 cell line using a costain of Erbitux-compound 7 conjugate and LysoTracker.

FIG. 13-1 shows fluorescent imaging of RBL-2H3 cell degranulation induced by the addition of ionomycin ((a): bright-field image, (b): fluorescent image).

FIG. 13-2 shows changes in fluorescent intensity (sites labeled "Roi") during granulation.

FIG. 14-1 is a fluorescent image of hippocampal cells labeled with Compound 3 prior to the application of electrical stimulation.

FIG. 14-2 is a magnified image showing visualized synaptic vesicle exocytosis induced via the application of electrical stimulation (200 AP, 10 Hz), and subsequent endocytosis.

FIG. 14-3 shows changes over time in the relative fluorescent intensity of synaptic vesicles.

FIG. 15 is a graph of the difference ($F_5-F_0$) between fluorescence value ($F_0$) after the addition of compound 3 and 17-AAG or DMSO and fluorescence value ($F_5$) after culturing for five hours.

DETAILED DESCRIPTION OF CERTAIN ILLUSTRATIVE EMBODIMENTS

Figure 5:
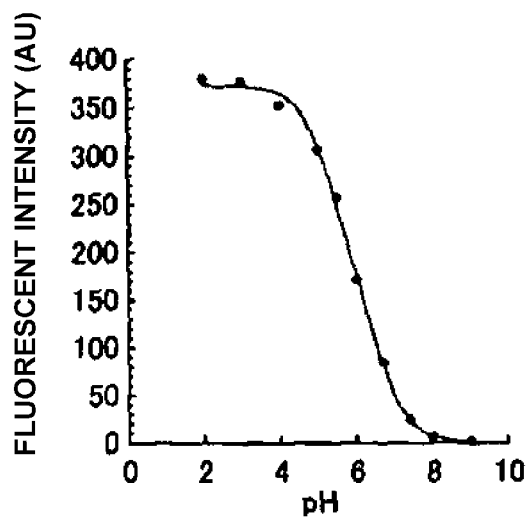

In the present invention, the compound or salt thereof represented by general formula (I) functions as an acidic environment-detecting fluorescent probe that only exhibits strong fluorescence in acidic environments.

In formula (I), $R_1$ and $R_2$ each independently represent hydrogen or an optionally substituted alkyl group, with at least one of $R_1$ and $R_2$ being an optionally substituted alkyl group. "Alkyl group" refers to a straight-chain alkyl group, branched-chain alkyl group, cyclic alkyl group, or combination thereof having 1-12 carbon atoms, preferably 1-6 carbon atoms, more preferably 1-4 carbon atoms. Preferred specific examples of alkyl groups include lower $C_{1-6}$ alkyl groups, such as methyl groups, ethyl groups, n-propyl groups, isopropyl groups, cyclopropyl groups, n-butyl groups, sec-butyl groups, isobutyl groups, tert-butyl groups, cyclopropyl methyl groups, n-pentyl groups, and n-hexyl groups.

The alkyl groups of $R_1$ and $R_2$ are optionally substituted, there being no particular limitation upon the substituent as long as it does not exhibit fluorescence properties; examples include halogen atoms, hydroxyl groups, alkoxyl groups, amino groups, carboxyl groups, sulfo groups, and alkylsulfonate groups. In the present invention, a 3,3,3-trifluoropropyl group, a 3,3-difluoropropyl group, and a 3-fluoropropyl group are especially preferable substituent-comprising alkyl groups.

In formula (I), $R_3$, $R_4$, $R_5$, $R_6$, $R_7$, and $R_8$ each independently represent hydrogen, a halogen, or an optionally substituted alkyl group. The types of alkyl groups and their substituents are similar to those disclosed for $R_1$ and $R_2$ above.

In formula (I), X represents a functional group into which a labeling site or a target-accumulating site can be introduced, or a substituent into which a labeling site or a target-accumulating site has been introduced. Moreover, in formula (I), m represents an integer from 0 to 5 and X may optionally be identical or different if there are two or more instances of m. m is preferably 1 or 2.

In formula (I), Y represents a halogen, an optionally substituted alkyl group, an optionally substituted alkoxyl group, or a cyano group. n represents an integer from 0 to 5, and Y may optionally be identical or different if there are two or more instances of n. The sum of m and n is an integer equal to 5 or less.

Embodiments of the compound according to the formula (I) represented by formula (I) include (1) one in which m=0 and n=0, i.e., the phenyl group of formula (I) does not comprise a substituent, and (2) one in which m=0, and n is 1 or greater, i.e., the phenyl group of formula (I) is a halogen, an optionally substituted alkyl group, an optionally substituted alkoxyl group, or a cyano group. Compounds encompassed by these embodiments have Rhodamine as a core and have an N-alkyl piperidinyl group introduced into their molecules, and only exhibit strong fluorescence in intracellular acidic environments, making them advantageously usable as fluorescent probes.

A preferred embodiment of the compound represented by formula (I) of the present invention is (3) one in which m is 1 or greater, and X is a functional group into which a labeling site or a target-accumulating site can be introduced. In this embodiment, n may be 0, 1, or greater, and m is more preferably 1 or 2. As will be discussed below, the introduction of a labeling site or a target-accumulating site into the molecule of the compound of formula (I) enables measurement of the pH dynamics within acidic organelles; thus, the inclusion of at least one functional group into which a labeling site or a target-accumulating site can be introduced for X is preferable, as this will allow for the design of a fluorescent probe matching the cellular phenomena being observed.

In the context of X in formula (I), a functional group into which a labeling site or a target-accumulating site can be introduced is a functional group that is capable of reacting with a labeling site or target-accumulating site, examples of which include a carboxyl group, a carboxyl group-comprising alkyl group, an ester group, an alkyl ester group, an amino group, an amide group, an alkylamino group, an isothiocyanate group, a sulfonyl chloride group, a haloalkyl group, a haloacetamide group, an azide group, and an alkynyl group, with a carboxyl group or a carboxyl group-comprising alkyl group being especially preferable.

An example of another preferred embodiment of the compound represented by formula (I) of the present invention is (4) one in which m is 1 or greater, and X is a substituent into which a labeling site or a target-accumulating site has been introduced. In this context, "substituent into which a labeling site or a target-accumulating site has been introduced" refers to all substituents in which a labeling site or target-accumulating site is introduced mediated by a functional group into which a labeling site or a target-accumulating site can be introduced. A typical substituent into which a labeling site or a target-accumulating site has been introduced can be represented by —(X'-T-S) (X' representing a group into which a labeling site or target-accumulating site is introduced, T, if present representing a crosslinking group, and S representing a labeling site or target-accumulating site). Here, m is preferably 1 or 2. The compound or salt thereof of this embodiment only exhibits strong fluorescence in acidic environments, can be labeled by a specific protein or the like, and can be localized within acidic organelle cells, enabling the visualization of various intracellular acidic vesicle-related phenomena in real-time. Compounds in which a labeling site or target-accumulating site has been introduced into part of a functional group into which a labeling site or a target-accumulating site can be introduced, i.e., a compound comprising both a functional group into which a labeling site or a target-accumulating site can be introduced and a substituent into which a labeling site or a target-accumulating site has been introduced, are encompassed by embodiment (4) of the present invention.

In the formula —(X'-T-S), X' represents a group into which a labeling site or target-accumulating site is introduced, examples of which include a carbonyl group, an alkyl carbonyl group, an ester group, an alkyl ester group, an amino group, an alkylamino group, an amide group, an isothiocyanate group, a sulfonyl chloride group, a haloalkyl group, a haloacetamide group, an azide group, and an alkynyl group, with a carbonyl group or an alkyl carbonyl group being especially preferable.

In the formula —(X'-T-S), T, if present, represents a crosslinking group, and may be any crosslinking group that functions as a spacer joining X' and S, Non-limiting examples include a substituted or non-substituted hydrocarbon group (an alkane, alkene, alkyne, cycloalkane, aromatic hydrocarbon, or the like), ethylene glycol group, diethylene glycol group, triethylene glycol group, or heterocyclic group (such as a piperidinyl group). The crosslinking group may optionally comprise, at one or both terminals, a functional group capable of joining X' and S, examples of such functional groups including an amino group, a carbonyl group, a carboxyl group, or an amide group.

In the formula —(X'-T-S), S represents a labeling site or target-accumulating site, examples of which include an N-hydroxysuccinimide ester, a HaloTag ligand (such as a 2-(2-((6-chlorohexyl)oxy)ethoxy)ethane amino group), a weakly basic amine, maleimide, an isothiocyanate group, a sulfonyl chloride group, a haloalkyl group, a haloacetamide group, an azide group, an alkynyl group, a benzylguanine derivative, or a benzylcytosine derivative. The labeling site or target-accumulating site of S also encompasses polyethylene glycol groups optionally comprising a modifying group at one or both terminals, examples of modifying groups including an amino group, a carbonyl group and a carboxyl group. A non-limiting example of polyethylene glycol groups comprising a modifying group is 3-(2-(2-(2-aminoethoxy)ethoxy)ethoxy)propanoic acid.

One preferred embodiment of the present invention is a compound or salt thereof represented by the following formula (II).

[Formula 2]

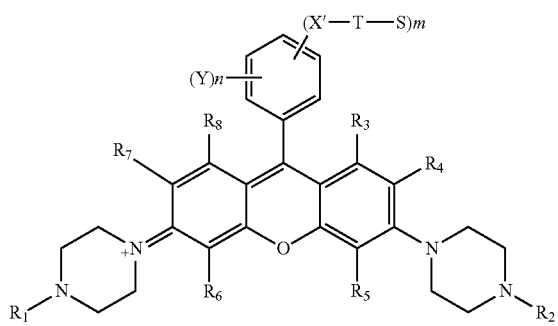

(II)

(wherein $R_1$-$R_8$ mean the same as in formula (I); X' represents a group into which a labeling site or target-accumulating site is introduced; T, if present, represents a crosslinking group; S represents a labeling site or target-accumulating site; Y means the same as in formula (I); m represents an integer from 1 to 5; —(X'-T-S) may optionally be identical or different if there are two or more instances of m; n represents an integer from 0 to 5; Y may optionally be identical or different if there are two or more instances of n; and the sum of m and n is an integer equal to no more than 5).

In formula (II), m is preferably 1 or 2.

The embodiment (4) of the compound represented by formula (I) or the compound represented by formula (II) can be labeled by a specific protein or the like, and can be localized within acidic organelle cells, enabling the visualization of various intracellular acidic vesicle-related phenomena in real-time. A non-limiting example thereof, in a case in which an N-hydroxysuccinimide ester is introduced into the molecular as a labeling site, is labeling the labeling site with the polysaccharide dextran, thereby the fluorescent probe according to the present invention to be localized within intracellular acidic vesicles. If a weakly basic amine is introduced into the molecule as a target-accumulating site, the fluorescent probe according to the present invention can be accumulated within acidic vesicles. If a HaloTag ligand is introduced as a labeling site, the HaloTag can be specifically labeled. Specifically, synaptic vesicles can be specifically labeled with the fluorescent probe by expressing a protein (VAMP2-HaloTag) in which a HaloTag is fused to the synaptic vesicle marker VAMP2 in neurons, and adding a fluorescent probe according to the present invention into which a HaloTag ligand has been introduced.

The compounds according to the present invention represented by formulas (I) and (II) may be present in the form of an acid addition salt or a base addition salt. Examples of acid addition salts include mineral acid salts such as hydrochlorides, sulfates, and nitrates, and organic acid salts such as methane sulfonates, p-toluene sulfonates, oxalates, citrates, and tartrates; and examples of base addition salts include metal salts such as sodium salts, potassium salts, calcium salts, and magnesium salts, and organic amine salts such as ammonium salts or triethylamine salts. Apart from these, a salt may be formed with an amino acid such as glycine. The compound or salt thereof according to the present invention may, in some instances, be present in the form of a hydrate or a solvate, which substances also fall within the scope of the present invention.

The compounds represented by formulas (I) and (II) of the present invention may, depending on the substituent type, comprise one or more asymmetric carbon atoms, and optically active substances based on one or more asymmetric carbon atoms and stereoisomers such as diastereomers based on two or more asymmetric carbon atoms, as well as arbitrarily selected mixtures or racemic mixtures of stereoisomers, all fall within the scope of the present invention.

Methods of manufacturing typical compounds constituting compounds according to the present invention are described in detail in the examples of the present description. Accordingly, a person skilled in the art can, based on these descriptions, produce the compounds according to the present invention represented by general formulas (I) and (II) by selecting reaction feedstocks, reaction conditions, reaction reagents and the like as appropriate, and altering or modifying these methods as necessary.

The compounds of the present invention represented by general formulas (I) and (II) of the present invention are useful as fluorescent probes for detecting acidic environments. The compounds or salts thereof represented by general formulas (I) and (II) have the characteristic of being either substantially non-fluorescent or only weakly fluorescent in neutral or basic regions, but strongly fluorescent in acidic regions. Accordingly, the compounds or salts thereof according to the present invention represented by general formulas (I) and (II) are extremely useful as an acidic environment-detecting fluorescent probe for measuring acidic regions in living cells or tissues under physiological conditions. The compounds or salts thereof according to the present invention represented by general formulas (I) and (II) are also extremely useful in that they enable the uptake of cancer-treating antibodies into cancer cells to be visualized, and the downregulation of cancer-regulated receptors to be evaluated in a simple manner.

There is no particular limitation upon the method in which the fluorescent probe according to the present invention is used; the probe can be used in a manner similar to that of a known fluorescent probe. Ordinarily, the compounds or salts thereof represented by general formulas (I) and (II) may be dissolved in an aqueous medium such as physiological saline or a buffer solution, or a mixture of an aqueous medium and a water-miscible organic solvent such as ethanol, acetone, ethylene glycol, dimethyl sulfoxide, or dimethylformamide, the solution added to a suitable buffer solution containing cells or tissue, and the fluorescence spectrum measured. The fluorescent probe according to the present invention may be combined with a suitable additive for use in the form of a composition. For example, the probe can be combined with an additive such as a buffering agent, a dissolution adjuvant, or a pH modifier.

EXAMPLES

The present invention will be explained hereafter in greater detail with the aid of examples, but the present invention is not limited to these examples.

[Raw Materials and Measuring Methods]

(1) Raw Materials

For general chemical materials, the highest-grade products purchasable or obtainable from Aldrich Chemicals, Tokyo Kagaku Sangyo, and Kokusan Chemical were used without being refined.

(2) Measuring Apparatus

NMR spectra were measured using a JNM-LA 300 manufactured by JEOL Ltd. at 300 MHz for $^1$HNMR and 75 MHz for $^{13}$CNMR. Mass spectra were measured using a JMS-T100LC AccuTOF manufactured by JEOL Ltd. UV and visible spectra were measured using a JASCO V-550. Fluorescence spectra were measured using a JASCO FP-6500.

(3) HPLC

HPLC measurement was performed using an HPLC system comprising a pump (PU-2080, JASCO) and a detector (MD-2015, JASCO) provided with an Inertsil ODS-3 (10.0 mm×250 mm) column (GL Sciences).

(4) Optical Properties and Fluorescence Quantum Yield

In order to measure absorption and fluorescence spectra, a dye compound was dissolved in dimethyl sulfoxide (DMSO, fluorescent analysis-grade, Dojindo) to obtain 1 mM of standard solution. Using a UV-1650 PCUV/V spectrometer (Shimadzu) and an FP-6600 fluorescence spectrometer (JASCO), the optical properties of the dye compound in 200 mM of a sodium phosphate buffer solution containing 0.03% (v/v) DMSO as a cosolvent were measured. In order to determine fluorescence quantum yield ($\Phi_{fl}$), the value ($\Phi_{fl}$=0.65) of Rhodamine B in ethanol was used as a standard. The value was calculated according to the following formula.

$$\Phi_x/\Phi_{st}=[A_{st}/A_x][n_x^2/n_{st}^2][D_x/D_{st}]$$

st: standard; x: specimen
A: absorption at excitation wavelength
n: index of refraction
D: area under fluorescence spectrum at energy scale 1. Synthesis and Measurement of Optical Properties of Fluorescent Probe Represented by General Formula (I)

The compound numbers in the following examples correspond to the compound number in the following schemes.

Example 1

Synthesis of 1-(9-(2-carboxyphenyl)-6-(4-methyl-piperazine-1-yl)-3H-xanthene-3-ylidene)-4-methyl-piperazine-1-ium chloride (Compound A)

Compound A comprising a functional group into which a labeling site or a target-accumulating site can be introduced constituting one compound represented by formula (I) was synthesized according to the procedure of the following scheme 1.

Scheme 1

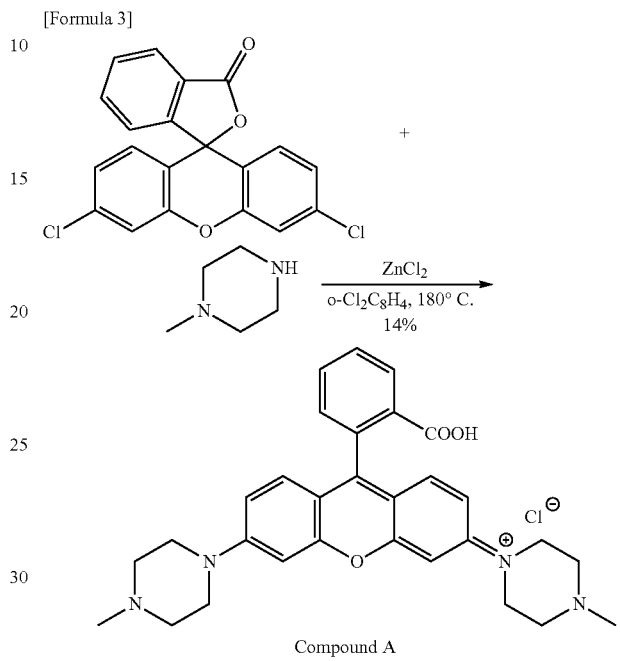

Compound A

3',6'-dichlorofluorane (228 mg, 0.575 mmol) and zinc chloride (784 mg, 5.75 mmol) were added to a flask, and argon substitution was performed. To this were added o-dichlorobenzene (1 mL) and N-methyl piperazine (1.28 mL, 11.5 mmol), and the mixture was stirred for one hour at 180° C. in an argon atmosphere. Next, the mixture was cooled to room temperature and DCM (30 mL) was added, after which the mixture was washed in a 2M aqueous solution KOH (30 mL) and dried using $Na_2SO_4$ anhydride, and the solvent was evaporated. The crude product was partially refined via column chromatography ($SiO_2$—$NH/CH_2Cl_2$:MeOH=99:1), then refined via HPLC(ODS-$C_{18}$, A (deionized water and 0.1% TFA):B ($CH_3CN$ and 0.1% TFA)=80:20 to 60:40; 30 minutes) to obtain 43.6 mg (14%) of a purple solid.

$^1$HNMR (300 MHz, $CDCl_3$) δ 2.35 (s, 6H), 2.54-2.56 (m, 8H), 3.25-3.27 (m, 8H), 6.58 (dd, 2H, J=2.2, 8.8 Hz), 6.63 (d, 2H, J=8.8 Hz), 6.69 (d, 2H, J=2.2 Hz), 7.14-7.17 (m, 1H), 7.59-7.64 (m, 2H), 7.99-8.01 (m, 1H)

HRMS (ESI$^+$): Calculated [M-Cl]$^+$ value: 497.25526; measured value: 497.25526 (D−0.01 mmu)

Example 2

Synthesis of 1-(9-(4-carboxyphenyl)-6-(4-methyl-piperazine-1-yl)-3H-xanthene-3-ylidene)-4-methyl-piperazine-1-ium (Compound 1)

Compound 1 constituting one compound represented by formula (I) was synthesized according to the procedure of the following scheme 2.

Scheme 2

[Formula 4]

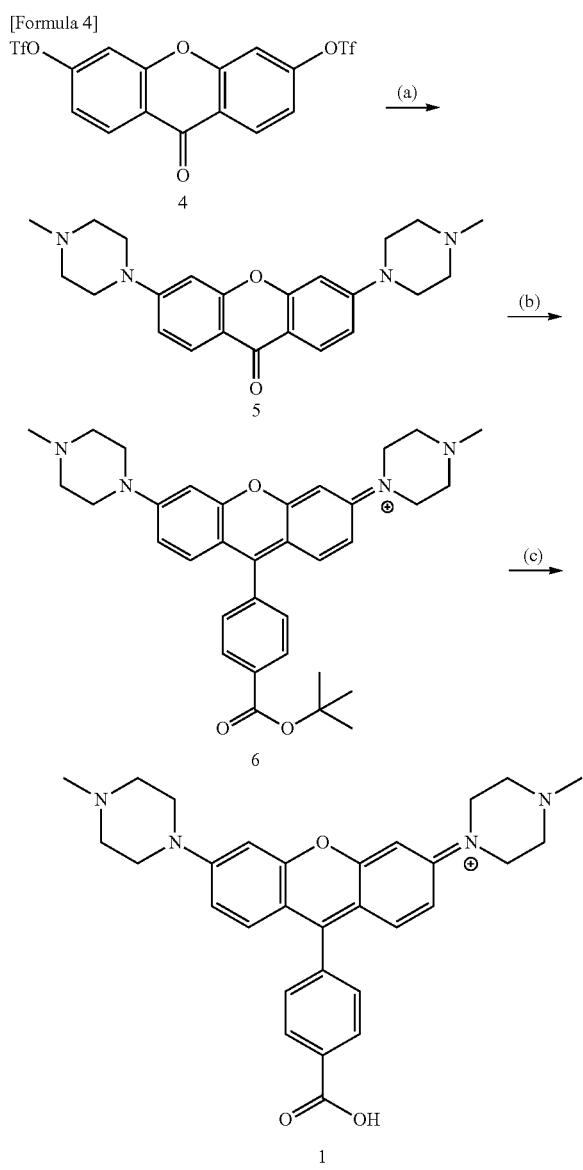

Reaction conditions: (a) N-methyl piperazine in dried dimethyl sulfoxide (DMSO), (b) tert-butyl-4-bromobenzoate in dried tetrahydrofuran (THF), sec-butyl lithium, (c) trifluoroacetic acid (TFA) in dichloromethane (DCM)

(1) Synthesis of 3,6-bis(4-methylpiperazine-1-yl)-9H-xanthene-9-one (Compound 5)

While stirring a dried DMSO (5 mL) solution of Compound 4 (9-oxo-9H-xanthene-3,6-dyl bis(trifluoromethane sulfonate)) (490 mg, 0.10 mmol), N-methylpiperazine (1.0 g, 10 mmol) was added thereto. The reaction mixture was stirred for 15 hours at 90° C. and precipitated using deionized water (10 mL). The precipitate was recovered, washed using a saturated aqueous solution of $NaHCO_3$ and water, and vacuum-dried. The crude product was refined via column chromatography ($SiO_2$—$NH/CH_2Cl_2$:MeOH=10:1) to obtain 306 mg (yield: 78%) of a yellow solid.

$^1$HNMR (300 MHz, $CDCl_3$, TMS): δ/ppm, 8.14 (d, $J_H$=9.6 Hz, 2H), 6.89 (d-d, $J_H$=2.1 Hz, $J_H$=9.6 Hz, 2H), 6.69 (d, $J_H$=2.1 Hz, 2H), 3.42 (m, 8H), 2.58 (m, 8H), 2.37 (s, 6H)

(2) Synthesis of Compound 1

Tert-butyl-4-bromobenzoate (108 mg, 0.39 mmol) and dried THF (5 mL) were added to a flame-dried flask that had been cleaned with argon. The solution was cooled to −78° C., 1M sec-butyllithium (0.5 mmol) was added thereto, and the mixture was stirred for five minutes. At the same temperature, Compound 5 (50 mg, 0.13 mmol) dissolved in dried THF (5 mL) was slowly added (over roughly 20 seconds), and the mixture was warmed to room temperature and stirred for one hour. 2N aqueous HCl solution (3 mL) was added to quench the reaction, and stirring was continued for five minutes at room temperature. A saturation aqueous $NaHCO_3$ solution (30 mL) was added thereto, and the whole was extracted using DCM (50 mL, three times). The organic solvent was washed in brine (50 mL) and dried using $Na_2SO_4$ anhydrate, the solvent was evaporated, and a crude product (150 mg) of Compound 6 (1-(9-(4-tert-butoxycarbonyl)phenyl)-6-(4-methylpiperazine-1-yl)-3H-xanthene-3-ylidene)-4-methylpiperazine-1-ium) was obtained in the form of a purple solid.

As a solution of the crude Compound 6 in DCM (3 mL) was stirred, TFA (3 mL) was added thereto at room temperature. The reaction mixture was stirred overnight at room temperature. The solvent was removed in a vacuum, and the residue was dissolved in water and acetonitrile and refined via HPLC(ODS-$C_{18}$, A (80% $CH_3CN$ and 100 mM triethylamine acetate buffer solution (pH 7.4)):B (100 mM triethylamine acetate buffer solution (pH 7.4))=20:80 to 40:60; 30 minutes) to obtain a 40 mg (62%) of a purplish-black solid.

$^1$HNMR (300 MHz, $CD_3OD$): δ/ppm, 8.20 (m, 2H), 7.48 (m, 4H), 7.28 (m, 2H), 7.20 (m, 2H), 3.80 (m, 8H), 2.62 (m, 8H), 2.37 (s, 6H)

$^{13}$CNMR (100 MHz, $CD_3OD$): δ/ppm, 173.7, 160.0, 158.6, 154, 1, 153.0, 133.3, 130.7, 130.4, 127.4, 116.3, 115.5, 98.7, 55.5, 47.9, 45.8

HR-ESI-MS: Calculated $[M]^+$ value for $C_{30}H_3N_4O_3$=497.2553; measured value: 497.2525

Example 3

The absorption spectrum and fluorescence emission spectrum when solution pH was altered from 2.0 to 10.0 for Compound A obtained in Example 1 were obtained according to the measurement method described above. Absorption spectra are shown in FIG. 1-1, fluorescence emission spectra in FIG. 1-2, and a pH profile showing pH-induced changes in fluorescent intensity in FIG. 1-3. The maximum absorption wavelength, maximum emission wavelength, fluorescent quantum yield, and pKa when pH is changed from 10.0 to 4.0 are shown in table 1.

TABLE 1

Table 1

| | Maximum Absorption Wavelength (nm) | Maximum Emission Wavelength (nm) | Fluorescence Quantum Yield | pKa |
|---|---|---|---|---|
| pH 4.0 | 527 | 554 | 0.961 | 5.4, |
| pH 10.0 | 547 | 575 | 0.024 | 6.8 |

Changing Compound A from a deprotonated type (pH 10.0) to a protonated type (pH 4.0) caused the maximum absorption wavelength to shift to a 20 nm shorter wavelength, and the protonated type (pH 4.0) had a fluorescent quantum yield exceeding 0.9. As shown in FIG. 1-3, it is apparent that Compound A exhibits changes of fluorescent from pH 4.5 to pH 6.0, making it useful as a fluorescent probe for detecting intracellular acidic environments.

Using a 100 mM phosphate buffer solution of Compound 1 (500 nM) obtained in Example 2, pH was altered from 4.39 to 9.24, and the fluorescence spectrum was measured. The obtained fluorescence emission spectrum and its pH profile are shown in FIG. 2. FIG. 2 shows that Compound 1 also exhibits fluorescence-increasing properties when the environment is changed from basic or neutral to acidic. Accordingly, it is apparent that Compound 1 is also useful as a fluorescent probe for detecting intracellular acidic environments.

2. Fluorescent Probe According to the Present Invention Marking a Polymer Such as a Protein, or a Target-Accumulating Site

Example 4

Synthesis of 1-(9-(2-(4-(((2,5-dioxopyrrolidine-1-yl)oxy) carbonyl)piperidine-1-carbonyl)phenyl)-6-(4-methylpiperazine-1-yl)-3H-xanthene-3-ylidene)-4-methylpiperazine-1-ium chloride (compound B)

Compound B in which N-hydroxysuccinimide ester was introduced into Compound A as a labeling site was synthesized according to the procedure of the following scheme 3 in order to impart a protein-labeling function.

Scheme 3

[Formula 5]

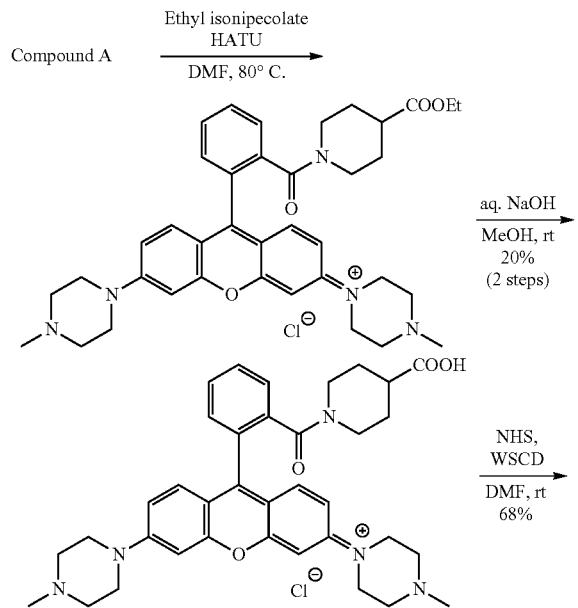

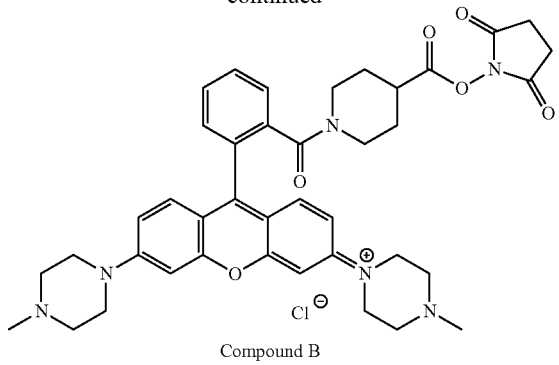

Compound B

Compound A (23.1 mg, 0.043 mmol) and ethyl isonipecotate (26.9 mg, 0.17 mmol) were dissolved in DMF (5 mL). To this was added 171 µL of a solution of 1M o-(benzotriazole-1-yl)-N, N,N',N'-tetramethyluronium hexafluorophosphate (HATU) in DMF, and the whole was heated to 80° C. in an argon atmosphere and stirred overnight. After solvent removal, the mixture was refined via HPLC(ODS-$C_{18}$, A (deionized water and 0.1% TFA): B ($CH_3CN$ and 0.1% TFA)=80:20 to 60:40; 30 minutes) to obtain 18.8 mg of a purple solid.

18.8 mg of purple solid so obtained was dissolved in methanol (10 mL) and stirred at room temperature. To this was added 240 µL of a 1M aqueous NaOH solution, the whole was stirred for 30 minutes at room temperature, and 120 µL of a 1M aqueous HCl solution was added. After solvent removal, the mixture was refined via HPLC(ODS-$C_{18}$, A (deionized water and 0.1% TFA):B ($CH_3CN$ and 0.1% TFA)=80:20 to 60:40; 30 minutes) to obtain 5.6 mg (2 steps: 20%) of a purple solid.

$^1$HNMR (300 MHz, $CDCl_3$) δ1.61-1.64 (m, 4H), 2.34 (s, 6H), 2.41 (m, 1H), 2.54-2.56 (m, 8H), 3.25-3.35 (m, 12H), 6.58 (dd, 2H, J=2.2, 8.8 Hz), 6.63 (d, 2H, J=8.8 Hz), 6.69 (d, 2H, J=2.2 Hz), 7.12-7.15 (m, 1H), 7.56-7.61 (m, 2H), 7.89-7.91 (m, 1H)

HRMS (ESI$^+$): Calculated [M-Cl]$^+$ value: 608.32368; measured value: 608.32334 (D−0.34 mmu)

Next, 5.6 mg of purple solid so obtained was dissolved in DMF (3 mL), 26 µL apiece of a 1M NHS DMF solution and a 1M WSCD DMF solution were added, and the whole was stirred overnight at room temperature. After solvent removal, the mixture was refined via HPLC(ODS-$C_{18}$, A (deionized water and 0.1% TFA):B ($CH_3CN$ and 0.1% TFA)=80:20 to 60:40; 30 minutes) to obtain 4.4 mg (68%) of a purple solid.

HRMS (ESI$^+$): Calculated [M-Cl]$^+$ value: 705.34006; measured value: 704.34391 (D 3.85 mmu)

Example 5

Synthesis of 1-(9-(4-((2-(dimethylamino)ethyl)carbonyl)phenyl)-6-(4-methylpiperazine-1-yl)-3H-xanthene-3-ylidene)-4-methylpiperazine-1-ium (Compound 2)

In order to effect accumulation with acidic vesicles, Compound 2 in which a weakly basic amine was introduced into Compound 1 as a target-accumulating site was synthesized according to the procedure of scheme 4 below.

Scheme 4

[Formula 6]

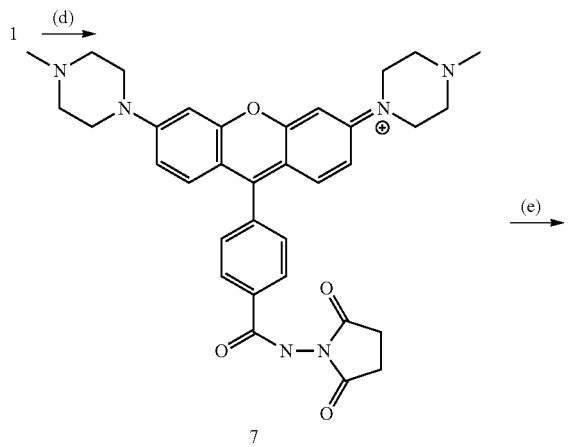

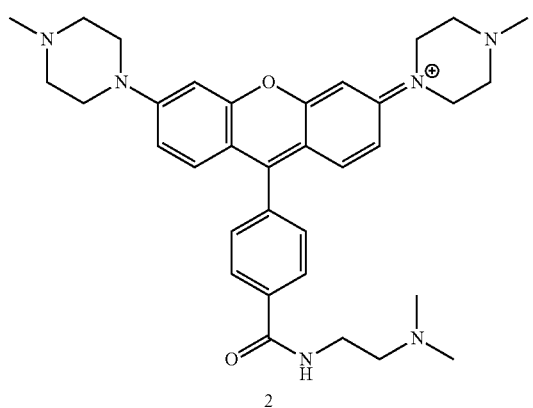

Reaction conditions: (d) (benzotriazole-1-yl oxy)-tris(dimethylamino)phosphonium hexafluorophosphate (BOP) in dried N,N'-dimethylformamide (DMF), N-hydroxysuccinimide (NHS), N,N'-diisopropylethylamine (DIPEA), (e) N,N'-dimethylethylenediamine in dried DMF, DIPEA Synthesis of Compound 2

While a solution of Compound 1 (1.5 mg, 3 μmol) in dried DMF (1 mL) was stirred, BOP (4 mg, 9 μmol), NHS (3 mg, 18 μmol), and DIPEA (3 μL, 18 μmol) were added thereto at room temperature. The reaction mixture was stirred for four hours in an argon atmosphere at 40° C., and the reaction was confirmed via HPLC (ODS-$C_{18}$, A ($CH_3CN$ and 0.1% TFA), B (deionized water and 0.1% TFA)=5:95 to 65:35; 30 minutes) and HR-ESI-MS (Compound 7: calculated $[M]^+$ value for $C_{34}H_{36}N_5O_5$=594.2716; measured value: 594.2681).

The solvent was evaporated, and the residue was redissolved in dried DMF (1 mL). While stirring this residue solution containing Compound 7, DIPEA (3 μL, 18 μmol) and N, N'-dimethylethylenediamine (3.0 mg, 30 μmol) were added thereto at room temperature. The reaction mixture was stirred for one hour in an argon atmosphere at 45° C. The solvent was removed in a vacuum, and the residue was dissolved in deionized water and acetonitrile and refined via HPLC (ODS-$C_{18}$, A ($CH_3CN$ and 0.1% TFA):B (deionized water and 0.1% TFA)=5:95 to 65:35; 30 minutes) to obtain 1.5 mg (88%) of a purplish-black solid.

$^1$HNMR (300 MHz, $CD_3OD$): δ/ppm, 8.19 (m, 2H), 7.65 (d, $J_H$=8.1 Hz, 2H), 7.52 (m, 2H), 7.40 (m, 4H), 4.11 (m, 8H), 3.84 (m, 2H), 3.34 (m, 10H), 3.02 (s, 6H), 2.96 (s, 6H)
$^{13}$CNMR (100 MHz, $CD_3OD$): δ/ppm, 169.8, 163.2, 160.3, 158.6, 154.1, 136.4, 133.4, 131.1, 129.2, 117.0, 116.3, 99.7, 58.6, 54.5, 53.9, 45.6, 43.7, 36.5
HR-ESI-MS: Calculated $[M]^+$ value for $C_{34}H_{43}N_6O_2$=567.3442; measured value 567.3443

Example 6

Synthesis of 2-methyl-1-(2-(3-(4-methylpiperazine-1-ium-1-ylidene)-6-(4-methylpiperazine-1-yl)-3H-xanthene-9-yl)phenyl)-1,4-dioxo-8,11,14-trioxa-2,5-diazaheptadecane-17-oate (Compound D)

Compound B in which N-hydroxysuccinimide ester was introduced into Compound A as a labeling site was synthesized according to the procedure of the following scheme 5.

Scheme 5

[Formula 7]

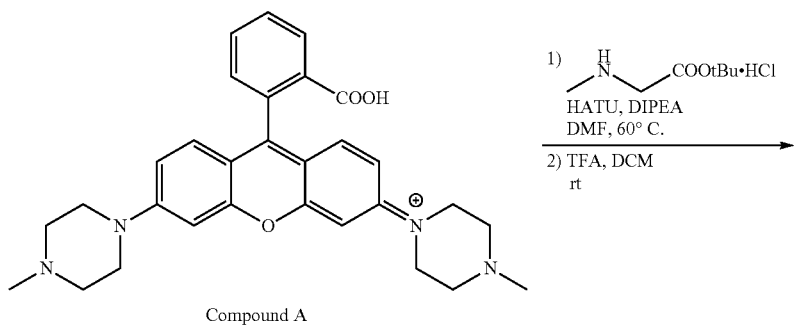

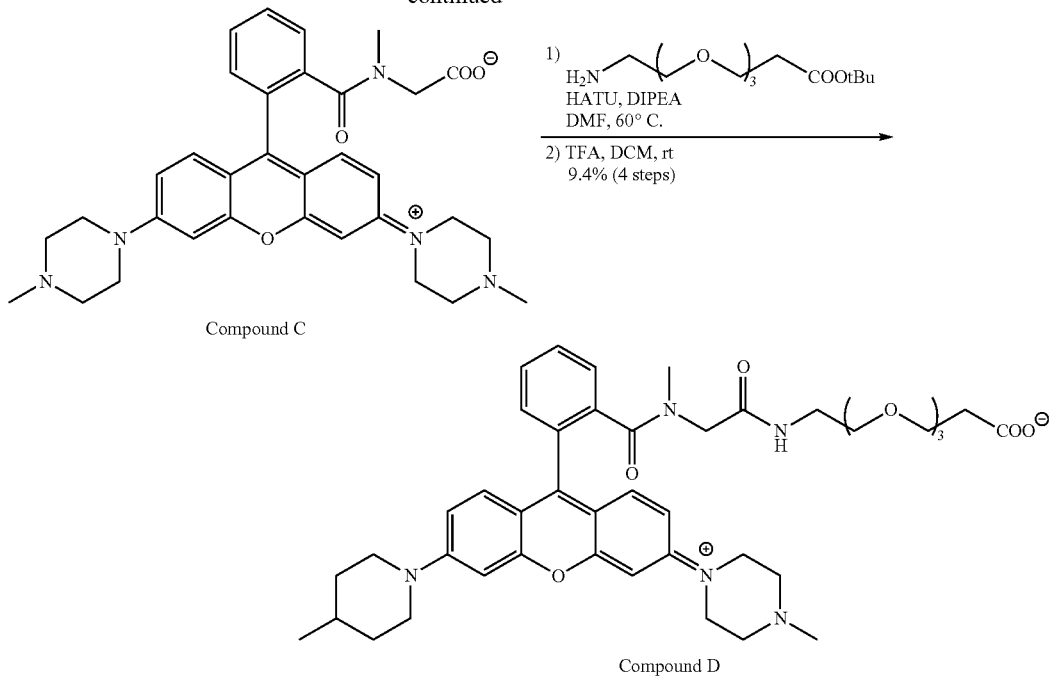

Compound C

Compound D

Compound A (35.7 mg, 71.7 μmol) and sarcosine tert-butyl ester hydrochloride (26.1 mg, 143 μmol) were dissolved in dried DMF (5 mL). HATU (54.6 mg, 54.7 μmol) and DIPEA (125 μL, 717 μmol) were added to the obtained solution. The obtained mixture was stirred for one day in an argon environment at room temperature. The solvent was removed in a vacuum, and, using 10% MeOH/DCM as an eluant, the residue was partially refined via preparatory HPLC to obtain a tert-butyl ester (78.7 mg) constituting Compound C. While a DCM solution of the crude compound was stirred, TFA (1 mL) was added thereto, and the reaction mixture was stirred overnight at room temperature. Sodium bicarbonate and water were added, and the obtained solution was stirred for several minutes. The aqueous layer was cleaned twice using DCM and concentrated. The residue was re-dissolved in MeOH, demineralized via filtration, and concentrated. The crude product was refined via HPLC (ODS-$C_{18}$, A (water and 0.1% TFA):B ($CH_3CN$ and 0.1% TFA)=99:1 to 1:99; 20 minutes) to obtain 11.5 mg (14%) of Compound C in the form of a purple solid. (LRMS (ESI$^+$): Calculated [M+H]$^+$ value: 568; measured value: 568)

Compound C (11.5 mg, 20.2 μmol) and HATU (15.4 mg, 54.7 μmol) were dissolved in DMF (2 mL). DIPEA (35.2 μL, 202 μmol) and tert-butyl 12 amino-4,7,10-trioxadodecanoate (theoretical value 80%) (14.0 mg, ≥40.3 μmol) were added to the obtained solution, and the obtained mixture was stirred in an argon atmosphere overnight at room temperature. The solvent was removed in a vacuum, and the residue was refined via HPLC (ODS-$C_{18}$, A (water and 0.1% TFA):B ($CH_3CN$ and 0.1% TFA)=99:1 to 1:99; 20 minutes) to obtain a tert-butyl ester constituting Compound D in the form of a red amorphous solid (LRMS (ESI$^+$): calculated [M+H]$^+$ value: 827; measured value: 827). While a DCM solution of the crude product so obtained was stirred, TFA (1 mL) was added thereto, and the reaction mixture was stirred at room temperature for three hours. The solvent was removed in a vacuum, and the residue was refined via HPLC(ODS-$C_{18}$, A (water and 0.1% TFA):B ($CH_3CN$ and 0.1% TFA)=99:1 to 1:99; 20 minutes) to obtain Compound D (5.2 mg; 9.4% over four steps) in the form of a red amorphous solid.

$^1$HNMR (400 MHz, $D_2O$) δ7.64-7.69 (m, 2H), 7.55-7.60 (m, 1H), 7.44-7.50 (m, 1H), 7.19 (d, 2H, J=9.6 Hz), 7.00 (dd, 2H, J=1.6, 9.6 Hz), 6.89 (d, 2H, J=1.6 Hz), 3.35-3.63 (m, 21H), 3.26 (t, 2H, J=5.2 Hz), 3.00 (t, 2H, J=5.2 Hz), 2.70 (s, 2H), 2.49 (m, 8H), 2.25-2.29 (m, 2H), 2.16 (s, 6H). (LRMS (ESI$^+$): Calculated [M+H]$^+$ value: 771; measured value: 771)

Evaluation of optical properties of Compound D The pH profile of the fluorescent intensity of Compound D is shown in FIG. 3. Compound D, like Compound A, was confirmed to exhibit pH sensitivity, with a pKa of 5.3 and 6.6.

Evaluation of Optical Properties of Marked Fluorescent Probe

Example 7

(1) Labeling Dextran Using Compound B

Using Compound B obtained in Example 4, in which N-hydroxysuccinimide ester was introduced into Compound A as a labeling site, dextran was labeled according to the following method.

Compound B and Alexa Fluor® 488 NHS ester (Molecular Probes) were each dissolved in DMSO to obtain 10 mM of a standard solution. Aminodextran (molecular weight: 10,000; Molecular Probes) was dissolved in 200 mM of a sodium phosphate buffer solution (pH 8.5) to obtain a 3.0 mg/mL (300 nmol/mL) standard solution. 4 equivalent weight of DMSO solutions of each of Compound B and Alexa Fluor® 488 NHS ester were added to 500 μL of a dextran standard solution. The obtained reaction solution was slowly mixed, and incubated in a dark place at ambient temperature for 60 minutes. Next, using a PD-10 column (GE Healthcare) and PBS (pH 7.4; GIBCO) as an eluant, dye conjugate 1 (also referred to hereafter as "Dex-compound B&A 488") was separated from the unlabeled dye.

(2) Evaluation of Optical Properties of Dye Conjugate 1 (Dex-Compound B&A 488)

Observation of fluorescence colors accompanying changes in pH in Dye Conjugate 1 obtained as described above revealed changes in fluorescence color due to changes in pH (not shown). FIGS. 4-1 to 4-5 show the results of measuring absorption spectrum, fluorescence emission spectrum, and fluorescence excitation spectrum when specimen solution pH is altered from 9.0 to 2.0. The pH profile for fluorescent intensity (FI) is shown in FIG. 5. A fitted curve for the pH profile was obtained according to the following formula.

$$FI = \frac{A + B \cdot 10^{pH-pK_{a1}} + C \cdot 10^{2 \cdot pH - pK_{a1} - pK_{a2}}}{1 + 10^{pH-pK_{a1}} + 10^{2 \cdot pH - pK_{a1} - pK_{a2}}}$$ [Numerical formula 1]

($pK_{a1} < pK_{a2}$)
(A, B, C: constants)

It was confirmed from FIG. 5 that dye conjugate 1, like Compound A, exhibits pH sensitivity. pKa was 5.3 and 6.5. The compound according to the present invention is believed to be capable of marking polymers such as dextran without a loss in the pH sensitivity of the compound.

Whereas the fluorescent intensity of Compound A contained in Dye Conjugate 1 is dependent upon pH, the fluorescent intensity of Alexa Fluor® 488 is not dependent upon pH; thus, by finding the ratio of the fluorescent intensities (specifically, fluorescent intensity at 540 nm/fluorescent intensity at 488 nm) of the two, it is possible to calculate the pH of the environment in which the dye conjugate 1 is contained.

Figure 6:
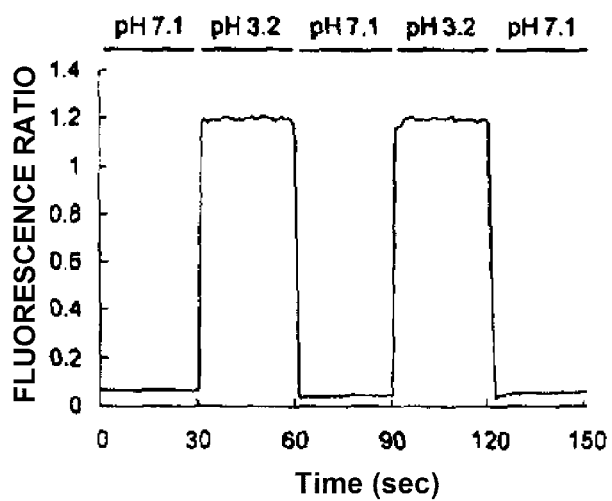
FIG. 6 shows changes in fluorescent intensity ratio due to cyclic changes in pH (pH alternated between 7.1 and 3.2 every 30 seconds).

Next, in order to investigate the reversibility of pH changes in Dye Conjugate 1, the fluorescent intensity ratio (fluorescent intensity at 540 nm/fluorescent intensity at 488 nm) was calculated for a case in which pH was cycled between 7.1 and 3.2 every 30 seconds. Results are shown in FIG. 6. It is apparent from FIG. 6 that Dye Conjugate 1 reversibly exhibits rapid responsiveness to pH changes, allowing for the rapid capturing of pH changes as fluorescent intensity ratio.

Visualizing Phenomena in Intracellular Acidic Vesicle Using Marked Fluorescent Probe Example 8

(A) Measurement of pH Dynamics within Acidic Organelles

Dye Conjugate 1, in which dextran is labeled using the fluorescent probe according to the present invention, can be localized within intracellular acidic vesicles. Using the dye conjugate 1, imaging of acidic organelles within HeLa cells was performed according to the following procedure.

(1) Cell Culture

HeLa cells were cultured in DMEM containing 10% fetal bovine serum, 100 U/mL penicillin, and 100 μg/mL streptomycin. All cell culture reagents were purchased from GIBCO. The cell line was maintained in an air atmosphere containing 5% $CO_2$ at 37° C.

(2) Observing Confocal Image of Dye Conjugate 1 Taken Up by HeLa Cells

HeLa cells ($4 \times 10^4$) were placed on an 8-welled plate (NUNC), and cultured overnight at 37° C. using 10% FBS-containing DMEM in an air atmosphere containing 5% $CO_2$. This medium was replaced with a medium containing 0.4 mg/mL of Dye Conjugate 1. After the cells were cultured for four hours, the solvent containing the dye conjugate 1 was removed, and DMEM containing 10% FBS was added. Following 16 hours of culturing, the cells were washed twice with PBS (pH 7.4) to obtain HeLa cells labeled with dye conjugate 1 (hereafter also referred to as "dye conjugate 1-labeled HeLa cells"), and the cells were observed using a confocal microscope. The cells were imaged using a TCSSP5 and a Leica Application Suite Advanced Fluorescene (LAS-AF) equipped with a ×60 objective lens to obtain a differential interference contrast (DIC) image and a fluorescent image. A white laser was used as the light source. The excitation wavelength and emission wavelength are shown in the figures. The obtained results are shown in FIG. 7.

Figure 7:
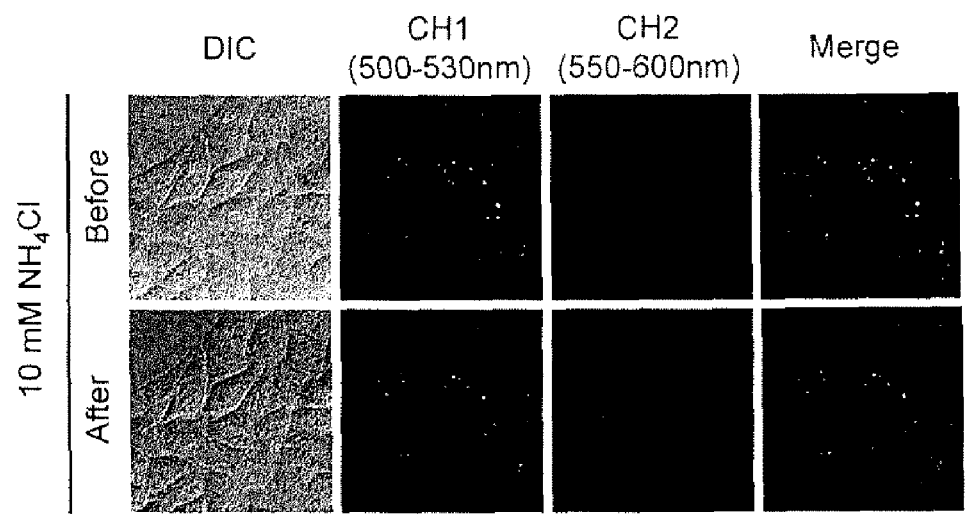
FIG. 7 shows imaging of (DIC images and fluorescent images) of dye conjugate 1-labeled HeLa cells.

The upper half of FIG. 7 shows the results of observing the dye conjugate 1-labeled HeLa cells obtained as described above, and the lower half shows observation results after the addition of 10 mM $NH_4Cl$, which is capable of neutralizing intracellular acidic environments, to the cells. The leftmost column (labeled "DIC") is a confocal image of the dye conjugate 1-labeled HeLa cells, the second-to-left column (labeled "CH1") is a fluorescent image at a fluorescence wavelength of 500-530 nm derived from Alexa 488, the second-to-right column (labeled "CH2") is a fluorescent image at an excitation wavelength of 550-600 nm derived from Compound B, and the rightmost column (labeled "Merge") is a fluorescent image combining CH1 and CH2. It is apparent from FIG. 7 that the fluorescent image derived from Compound B is drastically reduced by the addition of $NH_4Cl$.

Next, using the antibiotic Nigericin, which is known to function as a $H^+$, $K^+$ ionophore, and a high-concentration $K^+$ buffer, fluorescent intensity ratio and pH in situ calibration were performed according to the following procedure.

(3) In Situ pH Calibration and Calculation of pH within Cellular Vesicles

Figure 8:
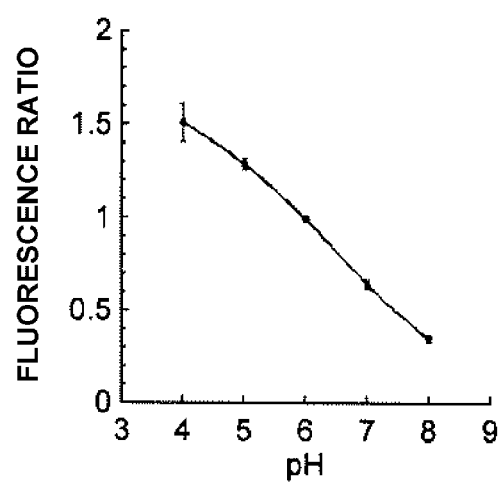
FIG. 8 is an in situ pH calibration curve for dye conjugate 1-labeled HeLa cells.

Ratiometric imaging of dye conjugate 1-labeled HeLa cells cultured in a high $K^+$ pH buffer solution (containing 130 mM KCl, 200 mM sodium phosphate) in the presence of 10 μM Nigericin was performed to obtain an in situ pH calibration curve (FIG. 8). For each of the pH points on the curve, images of 10 labeled vesicles from at least three cells were obtained for the sake of quantitative ratiometric analysis. On the basis of the obtained calibration curve, pH within cell vesicles (lysosomes) was calculated via ratiometric imaging of cells before and after treatment with 10 mM $NH_4Cl$. Results are shown in FIG. 9. FIG. 9 is a histogram of calculated pH values for individual lysosomes (n=10) before and after $NH_4Cl$ treatment. It is apparent from the figure that there is a dramatic change in lysosome pH distribution before and after $NH_4Cl$ treatment.

No prominent light-induced fading was observed in real-time lysosome imaging using the dye conjugate 1 even after extend periods of observation, showing that the dye conjugate 1 possessed high resistance to light-induced fading.

It was thus shown that using the fluorescent probe according to the present invention enables measurement of the pH within acidic organelles.

Example 9

(B) Visualization of Uptake of Cancer-Treating Antibodies into Cancer Cells

Erbitux (cetuximab), an antibody to the EGFR reception known to be overexpressed in cancer, specifically binds to EGFR, after which it is transported to intracellular acidic vesicles along with the EGFR, inducing EGFR downregulation and exhibiting therapeutic effects. It is believed that marking Erbitux with Compound 7 increases the fluorescence of Compound 7 when the Erbitux binds to EGFR and is transported to the intracellular acidic vesicles. The following experiment was performed on the assumption that capturing changes in fluorescent intensity of this sort will enable imaging of the manner in which the uptake of drug action-related cancer-treating antibodies into cancer cells occurs spatiotemporally.

(1) Labeling of Erbitux with Compound 7

5.0 mg/mL of injectable Erbitux (Merck Serono) was refined using a PD-10 column (GE Healthcare) with PBS (−) pH 7.4 (GIBCO) as an eluate to remove glycine and other contained additives. Using 200 mM of a sodium phosphate buffer solution (pH 10) (NaPi buffer solution), the liquid extract was prepared to create 2.5 mg/mL Erbitux/PBS (−)/NaPi solution with pH 8.5. 4 mM of Compound 7 was added to the 2.5 mg/mL Erbitux/PBS (−)/NaPi solution to yield a final concentration of 62 µM. The mixture was left standing at room temperature for one hour, a PD-10 column was used to convert the eluted solution to PBS (−) pH 7.4, and the Erbitux-compound 7 conjugate (10 µM; marked with an average of 3.83 units of Compound 7 per one molecule of Erbitux) was isolated. The fluorescence of the Erbitux-compound 7 conjugate increased as acidity increased (FIG. 10). pKa was 5.3 and 6.5. The compound according to the present invention is believed to be capable of marking polymers such as antibodies without a loss in the pH sensitivity of the compound.

(2) Confocal Fluorescent Imaging Using Erbitux-Compound 7 Conjugate

An experiment was performed on the EGFR-overexpressing A431 cell line under the following conditions using the Erbitux-compound 7 conjugate, for which increases in fluorescent intensity in response to acidic pH changes accompanying endocytosis following uptake into cells.

A431 was cultured in a medium of DMEM (GIBCO) containing 10% FBS (GIBCO) and 1% penicillin-streptomycin in a Chamber Slide 8 well (ibid.) at a temperature of 37° C. in a 5% $CO_2$ atmosphere. The Erbitux-compound 7 conjugate was added to the medium to a final concentration of 50 nm, and culturing was continued at 37° C. in a 5% $CO_2$ atmosphere. When the Erbitux-compound 7 conjugate was added and culturing was performed for four hours, intracellular uptake of Erbitux-compound 7 conjugate was observed (FIG. 11). When costaining was performed using the acidic organelle marker LysoTracker® Green DND-26 (Molecular Probes), Erbitux-compound 7 conjugate was confirmed to be present along with LysoTracker® Green DND-26 fluorescence (FIG. 12). From the foregoing, it was possible for the Erbitux-compound 7 conjugate to emit fluorescence in low pH environments within acidic organelles in A431, allowing for the visualization of the uptake of the cancer-treating antibody Erbitux into cancer cells.

Example 10

(C) Visualization of Degranulation Allergic Response

Because Compound 2 contains a weakly basic amine within its structure, it accumulates in acidic vesicles, and becomes fluorescent in the acidic environments within the vesicles. It is believed that vesicles having undergone exocytosis lead to an extracellular environment having a physiological pH of 7.4, causing neutralization of the environment within the vesicles and extracellular expulsion of Compound 2, which weakens the fluorescence of Compound 2. The following experiment was performed on the assumption that capturing changes in fluorescent intensity of this sort will enable imaging of the manner in which exocytosis occurs spatiotemporally.

Using Compound 2, imaging of degranulation within RBL-2H3 cells using a mast cell model was performed. The RBL-2H3 cells were incubated (37° C.) for two hours in a medium containing 500 nM of Compound 2, then washed in the medium twice using an HBS buffer. To this was added 1 µM of ionomycin, thereby inducing degranulation, and fluorescent imaging was performed (FIG. 13-1). FIG. 13-1 (a) is a bright-field image, and (b) is a fluorescent image. In (b) (ii), the vesicles observable at sites Roi 1 and 2 in (i) have vanished, and, similarly, the vesicles observable at site Roi 3 in (i) and (ii) have vanished in (iii), and the vesicles observable at site Roi 4 in (i)-(iii) have vanished in (iv). The results of capturing this phenomenon as changes in fluorescent intensity are shown in FIG. 13-2. FIG. 13-2 shows changes in fluorescent intensity at each of the Roi sites, and it is apparent from the figure that there are dramatic reductions in the fluorescence observed in the acidic vesicles at respective timings following ionomycin addition. It is believed that degranulation was successfully detected as changes in fluorescent intensity using Compound 2 in this way.

3. Fluorescent Probe According to the Present Invention with Specific Protein-Labeling Site Introduced

Example 11

Synthesis of 1-(9-(4-((25-chloro-12-oxo-3,6,9,16, 19-pentaoxa-13-azapentacosyl)carbamoyl)phenyl)-6- (4-methylpiperazine-1-yl)-3H-xanthene-3-ylidene)- 4-methylpiperazine-1-ium (Compound 3)

Compound 3 formed by introducing a HaloTag ligand into Compound 1 was synthesized according to the procedure of scheme 6 below in order to enable the labeling of vesicle-associated membrane protein 2 (VAMP2) localized in synaptic vesicles using HaloTag technology.

Scheme 6
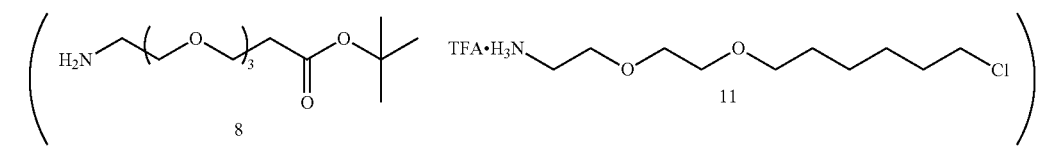
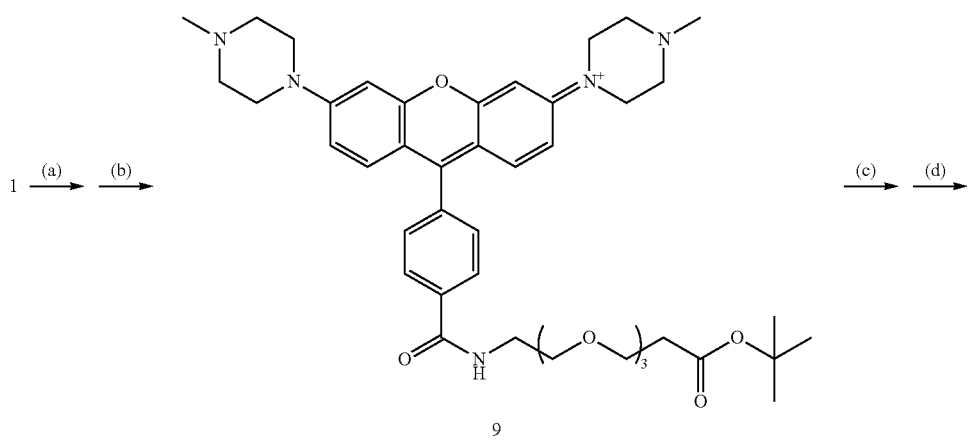
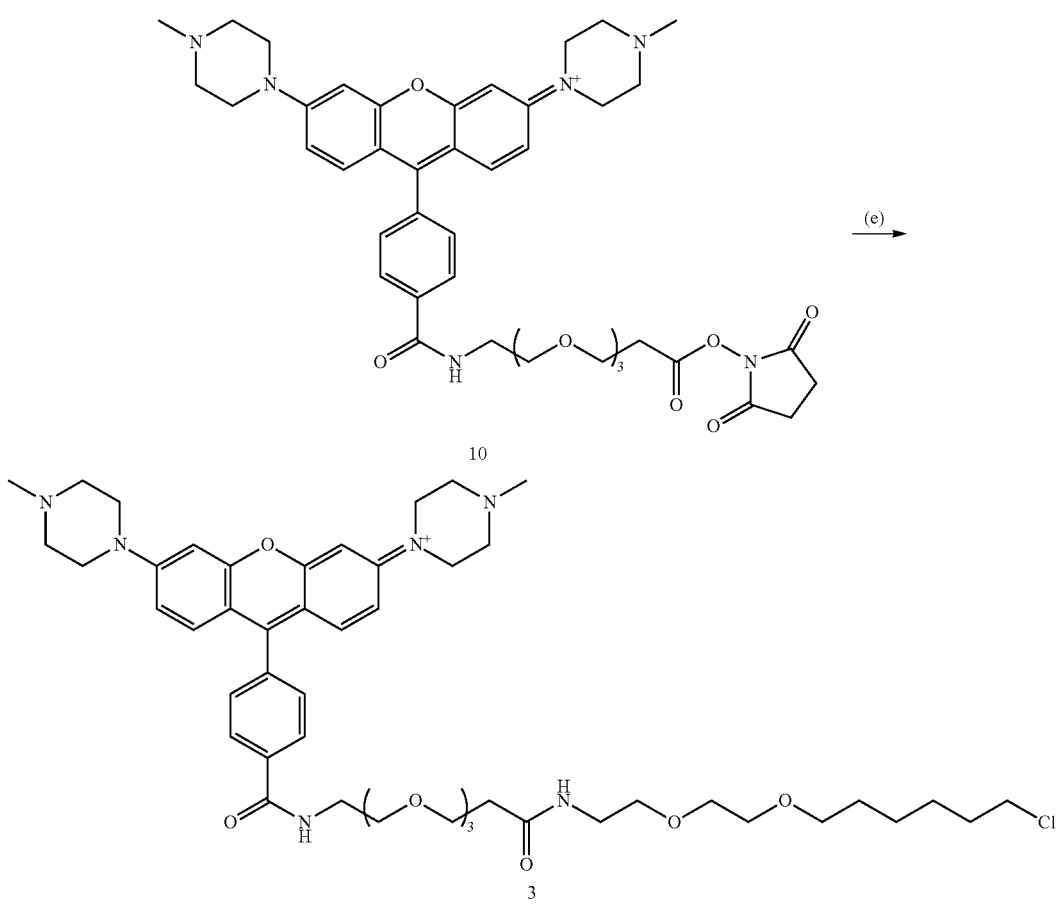

Reaction conditions: (a) BOP in dried DMF, NHS, DIPEA; (b) compound 8, DIPEA in dried DMF; (c) TFA in DCM; (d) 1-ethyl-3-(3-dimethyl aminopropyl)carbodiimide hydrochloride (WSC) in dried DMF, NHS; (e) Compound 11, DIPEA in dried DMF (1) Synthesis of 1-(9-(4-((14,14-dimethyl-12-oxo-3,6,9,13-tetraoxapentadecyl)carbamoyl)phenyl)-6-(4-methylpiperazine-1-yl)-3H-xanthene-3-ylidene)-4-methylpiperazine-1-ium (Compound 9)

While a solution of Compound 1 (35 mg, 70 μmol) in dried DMF (5 mL) was stirred, BOP (160 mg, 0.35 mmol), NHS (35 mg, 0.35 mmol), and DIPEA (240 μL, 0.70 mmol) were added thereto at room temperature. The reaction mixture was stirred for at 40° C. for two hours in an argon atmosphere, and a reaction was confirmed via HPLC and HR-ESI-MS as in the case of Compound 2.

The solvent was evaporated, and the residue was re-dissolved in dried DMF (2 mL). The solution of this Compound 7-containing residue was stirred, and DIPEA (240 μL, 0.70 mmol) and Compound 8 (tert-butyl 12-amino-4,7,10-trioxadodecanoate; Aldrich; 110 mg, 0.35 mmol) were added thereto at room temperature. The reaction mixture was stirred overnight at 40° C. in an argon atmosphere. The solvent was removed in a vacuum, and the residue was re-dissolved in deionized water and acetonitrile and refined via HPLC (ODS-$C_{18}$, A (80% $CH_3CN$ and 100 mM triethylamine acetate buffer solution (pH 7.4)):B (100 mM triethylamine acetate buffer solution (pH 7.4))=30:70-70:30; 30 minutes) to obtain 37 mg (70%) of a purplish-black solid.

$^1$HNMR (300 MHz, $CD_3OD$): δ/ppm, 8.15 (m, 2H), 7.70 (m, 2H), 7.43 (m, 2H), 6.93 (m, 2H), 6.69 (m, 2H), 3.81 (m, 2H), 3.69-3.50 (m, 20H), 2.62 (m, 8H), 2.44 (m, 2H), 2.35 (m, 6H), 1.45 (s, 9H)

HR-ESI-MS (NBA): Calculated [M]$^+$ value for $C_{43}H_{58}N_5O_7$=756.4336; measured value: 756.4311

(2) Synthesis of 1-(9-(4-((2-(2-(2-(3-((2,5-dioxopyrrolidine-1-yl)oxy)-3-oxopropoxy)ethoxy)ethoxy)ethyl)carbamoyl)phenyl)-6-(4-methylpiperazine-1-yl)-3H-xanthene-3-ylidene)-4-methylpiperazine-1-ium (Compound 10)

A solution of Compound 9 (37 mg, 49 μmol) in DCM (3 mL) was stirred, and TFA (3 mL) was added thereto at room temperature. The reaction mixture was stirred overnight at room temperature. The solvent was removed in a vacuum, the residue was suspended in toluene (3 mL), the solvent was evaporated, vacuum-drying was performed, and deprotected Compound 9 (40 mg) was obtained as a dark purple oil without further refining.

A solution of the deprotected Compound 9 (40 mg) in dried DMF (5 mL) was stirred, and WSC (94 mg, 0.49 mmol), NHS (49 mg, 0.49 mmol) and DIPEA (340 μL, 0.98 mmol) were added thereto at room temperature. The reaction mixture was stirred in an argon atmosphere at room temperature for five hours. The solvent was removed in a vacuum, and the residue was re-dissolved in deionized water and acetonitrile and purified via HPLC (ODS-$C_{18}$, A ($CH_3CN$ and 0.1% TFA):B (deionized water and 0.1% TFA)=15:85 to 30:70; 30 minutes) to obtain 25 mg (64%) of a dark purple solid.

$^1$HNMR (300 MHz, acetone-$d_6$): δ/ppm, 8.23 (m, 2H), 7.65 (m, 2H), 7.57-7.44 (m, 4H), 7.27 (m, 2H), 3.81 (m, 2H), 3.69-3.56 (m, 20H), 3.34 (m, 8H), 2.97 (m, 2H), 2.59 (s, 6H), 2.07 (s, 4H)

HR-ESI-MS: Calculated [M]$^+$ value for $C_{43}H_{53}N_6O_9$=797.3874; measured value: 797.3865

(3) Synthesis of Compound 3

A solution of Compound 10 (25 mg, 31 μmol) in dried DMF (2 mL) was stirred, and DIPEA (54 μL, 0.31 mmol) and Compound 11 (2-(2-((6-chlorohexyl)oxy)ethoxy)ethane amine 2,2,2-trifluoroacetate) (105 mg, 0.31 mmol) were added thereto at room temperature. The reaction mixture was stirred in an argon atmosphere at room temperature for ten hours. The solvent was removed in a vacuum, and the residue was re-dissolved in deionized water and acetonitrile and refined via HPLC (ODS-$C_{18}$, A (80% $CH_3CN$ and 100 mM triethylamine acetate buffer solution (pH 7.4)):B (100 mM triethylamine acetate buffer solution (pH 7.4))=20:80-80:20; 30 minutes) to obtain 15 mg (54%) of a purplish-black solid.

$^1$HNMR (300 MHz, $CD_3OD$): δ/ppm, 8.15 (m, 2H), 7.64 (m, 2H), 7.55 (m, 2H), 7.41 (m, 4H), 3.72-3.44 (m, 34H), 3.34 (m, 8H), 2.99 (s, 6H), 2.41 (T, $J_H$=6.6 Hz, 2H), 1.57 (m, 2H), 1.38 (m, 4H), 1.23 (m, 4H)

$^{13}$CNMR (75 MHz, $CD_3OD$): δ/ppm, 174.0, 154.4, 154.1, 153.3, 135.5, 133.0, 131.0, 127.9, 127.8, 114.8, 113.3, 102.7, 72.2, 71.6, 71.5, 71.4, 71.3, 71.2, 71.1, 70.5, 68.3, 68.2, 55.9, 52.3, 46.2, 46.1, 45.7, 40.9, 40.4, 37.6, 33.8, 30.8, 27.7, 26.5

HR-ESI-MS: Calculated [M]$^+$ value for $C_{49}H_{70}N_6O_8Cl_1$=905.4944; measured value: 905.4962

Example 12

Visualization of Synaptic Vesicle Membrane Transport

Because Compound 3 contains a HaloTag ligand within its structure, it is capable of HaloTag-specific labeling. Specific labeling of synaptic vesicles via Compound 3, which constitutes a fluorescent probe, can be performed by expressing a VAMP2-HaloTag protein in which a HaloTag is fused to the synaptic vesicle marker VAMP2 in neurons, and adding Compound 3 thereto. The following experiment was performed on the assumption that, because synaptic vesicles are ordinarily acidic, capturing changes in fluorescent intensity will enable imaging of the manner in which exocytosis occurs spatiotemporally.

A VAMP2-HaloTag was expressed in cultured hippocampal neurons, and incubation was performed at 37° C. for one hour using a K-HBS buffer containing 3 μM of Compound 3. The K-HBS buffer was exchanged for a medium, and incubation was performed at 37° C. for 15 minutes, after which the cells were washed once in medium and three times in HBS buffer. Neurotransmission was induced in the cultured neurons by applying electrical stimulation, and fluorescent imaging was performed (FIGS. 14-1 to 3).

FIG. 14-1 is a fluorescent image of hippocampal cells labeled with Compound 3 prior to the application of electrical stimulation, and FIG. 14-2 is a magnified image of the square-outlined section of FIG. 14-1 for the sake of visualizing synaptic vesicle exocytosis induced by the application of electrical stimulation (200 AP, 10 Hz), as well as the subsequent endocytosis. The fluorescence at sites Roi 1 and Roi 2 shown in the upper left image of FIG. 14-2 temporarily diminishes 20 seconds after the application of electrical stimulation (lower left image), but subsequent recovery was observed at these sites (lower right image). This phenomenon is also clearly shown by FIG. 14-3, which shows changes in fluorescent intensity before and after electrical stimulation (with the solid line indicating Roi 1, the dashed line indicating Roi 2, and electrical stimulation being applied at the time indicated by the arrow). Based on the observed changes in fluorescence, it is believed that, following exocytosis, synaptic vesicles are retaken back into cells via endocytosis.

Example 13

Evaluation of Drug-Induced Downregulation of the Cancer-Related Receptor HER2

Downregulation of the HER2 receptor, which is known to be overexpressed in cancer, exhibits therapeutic effects upon cancer. In order to perform a simple fluorescent evaluation of drug-induced, the HaloTag-comprising Compound 3 was added to cells in which were expressed an HER2-HaloTag protein in which a HaloTag was fused to HER2, and the target receptor HER2 was marked specifically with a fluorescent probe. Compound 3 marking the HER2 is believed to glow brightly only when transported to intracellular acidic vesicles during HER2 downregulation. The following experiment was performed on the assumption that capturing these changes in fluorescent intensity will allow for the simple evaluation of HER2 downregulation.

(1) Reagent and Cell Preparation

The pH-sensitive fluorescent probe Compound 3 and 17-AAG (Wako Pure Chemicals) were diluted with water. An equal amount of DMSO (Sigma-Aldrich) was added as a control for the 17-AAG. SKOV3 cells expressing the HER2-HaloTag were suspended in RPMI (Nacalai Tesque) containing 2% FBS (CCB), implanted in a 384-well imaging plate (PerkinElmer), and cultured overnight at 37° C. in a 5% CO2 atmosphere.

(2) High-Throughput Evaluation of HER2 Downregulation

Compound 3 and 17-AAG were added to 354 wells of a 384-well imaging plate implanted with SKOV3 cells expressing the HER2-HaloTag to respective final concentrations of 30 nm and 10 μM. DMSO alone was added to 32 wells instead of 17-AAG as a control. Fluorescence values at 580 nm induced by 535 excitation were measured using a plate reader, after which culturing was performed at 37° C. in a 5% $CO_2$ atmosphere for five hours, and fluorescence values were again measured using the plate reader. Calculation of differences in fluorescence values before and after culturing showed a large increase in fluorescence values in wells treated with 17-AAG (FIG. 15). In this way, it is possible to simply evaluate downregulation of the cancer-related receptor HER2 via fluorescence values.

What is claimed is:

1. A compound represented by the following general formula (I) or a salt thereof:

[Formula 1]

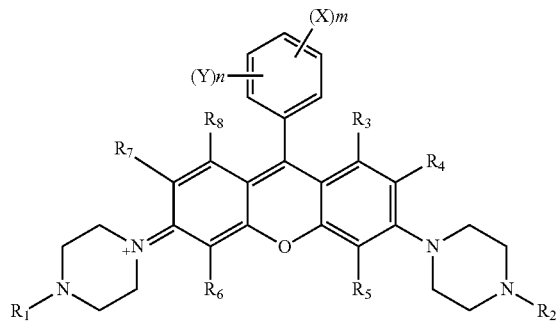

wherein $R_1$ and $R_2$ each independently represents hydrogen or an alkyl group that may be substituted with at least one substituent selected from the group consisting of halogen atom, hydroxyl group, alkoxyl group, amino group, carboxyl group, sulfo group, and alkylsulfonyloxy group (at least one of $R_1$ and $R_2$ being an alkyl group that may be substituted with at least one substituent selected from the group consisting of halogen atom, hydroxyl group, alkoxyl group, amino group, carboxyl group, sulfo group, and alkylsulfonyloxy group); $R_3$, $R_4$, $R_5$, $R_6$, $R_7$, and $R_8$ each independently represents hydrogen, a halogen, or an alkyl group that may be substituted with at least one substituent selected from the group consisting of halogen atom, hydroxyl group, alkoxyl group, amino group, carboxyl group, sulfo group, and alkylsulfonyloxy group; X represents a functional group into which a labeling site or a target-accumulating site can be introduced, or a substituent into which a labeling site or a target-accumulating site has been introduced, wherein the functional group into which a labeling site or a target-accumulating site can be introduced is a carboxyl group, or an alkyl group substituted with a carboxyl group, and wherein the substituent into which a labeling site or a target-accumulating site has been introduced is represented by —(X'-T-S) (X' represents a group into which a labeling site or target-accumulating site is introduced, wherein X' is a carbonyl group, an alkyl carbonyl group, or a carboxamido group; T, when present, represents a crosslinking group, wherein the crosslinking group is selected from the group consisting of a divalent hydrocarbon group, an ethylene glycol group, a diethylene glycol group, a triethylene glycol group, and a divalent piperidine ring group, and the crosslinking group optionally modified by a functional group selected from the group consisting of an amino group, a carbonyl group, a carbonyloxy group, and a carboxamido group at one or both terminals; and S represents a labeling site or target-accumulating site, wherein S is (2,5-dioxo-1-pyrrolidinyl)oxy, a 2-(2-((6-chlorohexyl)oxy)ethoxy)ethane amino group, a maleimido, an isothiocyanato group, a chlorosulfonyl group, a haloalkyl group, a haloacetamido group, an azido group, an alkynyl group and a polyethylene glycol group having not more than three ethoxy units and optionally substituted by a group selected from the group consisting of an amino group, a carbonyl group and a carboxyl group at one or both terminals; Y represents a halogen, an alkyl group that may be substituted with at least one substituent selected from the group consisting of halogen atom, hydroxyl group, alkoxyl group, amino group, carboxyl group, sulfo group, and alkylsulfonyloxy group, an alkoxyl group that may be substituted with at least one substituent selected from the group consisting of halogen atom, hydroxyl group, alkoxyl group, amino group, carboxyl group, sulfo group, and alkylsulfonyloxy group, or a cyano group; m represents an integer from 1 to 5; X may optionally be identical or different when m is 2 or higher; n represents an integer from 0 to 5; and Y may optionally be identical or different when n is 2 or higher and the sum of m and n being an integer equal to 5 or less.

2. The compound or salt thereof according to claim 1, wherein each of $R_1$ and/or $R_2$ in general formula (I) is a $C_{1-4}$ alkyl group that may be substituted with at least one substituent selected from the group consisting of halogen atom, hydroxyl group, alkoxyl group, amino group, carboxyl group, sulfo group, and alkylsulfonyloxy group.

3. The compound or salt thereof according to claim 1, wherein the compound is represented by the following formula:

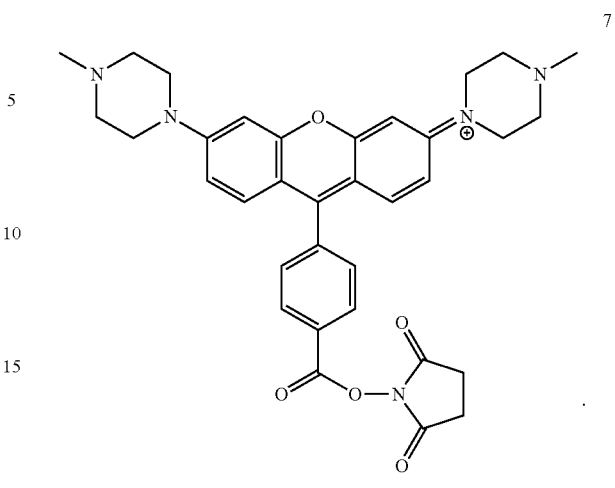

4. A fluorescent probe comprising the compound or salt thereof according to claim 1.

5. A method of measuring pH changes in intracellular acidic regions in living cells or tissues, the method comprising:
(a) introducing the compound or salt thereof according to claim 1 into a cell; and
(b) measuring fluorescence emitted within the cell by the compound or salt thereof.

6. The method according to claim 5, wherein acidic regions in which intracellular acidic organelles are present are measured.

* * * * *